US012779004B2

(12) United States Patent
Lin et al.

(10) Patent No.: US 12,779,004 B2
(45) Date of Patent: Nov. 3, 2026

(54) METHOD FOR HAIR CARE BY USING CASHEW TESTA EXTRACT

(71) Applicant: TCI CO., LTD., Taipei (TW)

(72) Inventors: Yung-Hsiang Lin, Taipei (TW); Fan-Jhen Dai, Taipei (TW); Huan-You Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 286 days.

(21) Appl. No.: 18/670,742

(22) Filed: May 22, 2024

(65) Prior Publication Data

US 2025/0000783 A1 Jan. 2, 2025

Related U.S. Application Data

(60) Provisional application No. 63/503,503, filed on May 22, 2023.

(51) Int. Cl.

| | |
|---|---|
| ***A61K 36/38*** | (2006.01) |
| ***A61K 8/9789*** | (2017.01) |
| ***A61K 9/00*** | (2006.01) |
| ***A61K 36/22*** | (2006.01) |
| ***A61P 17/14*** | (2006.01) |
| ***A61P 19/00*** | (2006.01) |
| ***A61P 29/00*** | (2006.01) |
| ***A61P 39/06*** | (2006.01) |
| ***A61Q 7/00*** | (2006.01) |

(52) U.S. Cl.

CPC ............ *A61K 36/38* (2013.01); *A61K 8/9789* (2017.08); *A61K 9/0095* (2013.01); *A61K 36/22* (2013.01); *A61P 17/14* (2018.01); *A61P 19/00* (2018.01); *A61P 29/00* (2018.01); *A61P 39/06* (2018.01); *A61Q 7/00* (2013.01); *A61K 2236/39* (2013.01); *A61K 2236/51* (2013.01); *A61K 2800/92* (2013.01)

(58) Field of Classification Search

None

See application file for complete search history.

(56) References Cited

U.S. PATENT DOCUMENTS

| | | | | |
|---|---|---|---|---|
| 12,568,974 | B2 * | 3/2026 | Gan | A01N 59/16 |
| 2020/0069759 | A1 * | 3/2020 | Rana | A61K 36/77 |
| 2021/0346477 | A1 * | 11/2021 | Spencer | C07K 14/70578 |

FOREIGN PATENT DOCUMENTS

| | | | | |
|---|---|---|---|---|
| JP | 2007070336 A | | 3/2007 | |
| WO | WO-2020046477 A1 | * | 3/2020 | A61P 17/00 |

OTHER PUBLICATIONS

Iqbal et al. (2021) JSTAR vol. No. 2, Issue No. 1 (9 pages). (Year: 2021).*

Salehi et al. (2020) Frontiers in Endocrinology vol. 11: Article 295 (16 pages). (Year: 2020).*

Srisuksomwong et al. (2023) Cosmetics 10, 17 (10 pages). (Year: 2023).*

7 Amazing Benefits of Cashew Nuts for Skin, Hair and Eyes, https://web.archive.org/web/20230131040657/https://www.herzindagi.com/diet-nutrition/amazing-benefits-of-cashew-nuts-for-skin-hair-eyes-article-131000.2023/01/31 Full text.

P. Sruthi, et al. Profiling of phenolics in cashew nut (*Anacardium occidentale* L.) testa and evaluation of their antioxidant and anti-microbial properties. Food Bioscience. vol. 51, Feb. 2023 Abstract.

* cited by examiner

*Primary Examiner* — Russell G Fiebig

(74) *Attorney, Agent, or Firm* — Chich-Mei Wang

(57) ABSTRACT

The present disclosure provides a method for hair care by using a cashew testa extract, which is used for preparing a hair care composition. The cashew testa extract is obtained by extracting a testa of cashew nut of *Anacardium occidentale* with a solvent.

11 Claims, 17 Drawing Sheets

Specification includes a Sequence Listing.

SEQUENCE LISTING

```
Sequence total quantity: 16
SEQ ID NO: 1            moltype = DNA  length = 20
FEATURE                 Location/Qualifiers
source                  1..20
                        mol_type = other DNA
                        organism = synthetic construct
SEQUENCE: 1
tacgggcatc ggtgcttaat                                              20

SEQ ID NO: 2            moltype = DNA  length = 20
FEATURE                 Location/Qualifiers
source                  1..20
                        mol_type = other DNA
                        organism = synthetic construct
SEQUENCE: 2
gccattgtac acgccaacag                                              20

SEQ ID NO: 3            moltype = DNA  length = 17
FEATURE                 Location/Qualifiers
source                  1..17
                        mol_type = other DNA
                        organism = synthetic construct
SEQUENCE: 3
tgccttcctt cgcggtg                                                 17

SEQ ID NO: 4            moltype = DNA  length = 23
FEATURE                 Location/Qualifiers
source                  1..23
                        mol_type = other DNA
                        organism = synthetic construct
SEQUENCE: 4
cacaaatgtc ctgtggaagt aat                                          23

SEQ ID NO: 5            moltype = DNA  length = 20
FEATURE                 Location/Qualifiers
source                  1..20
                        mol_type = other DNA
                        organism = synthetic construct
SEQUENCE: 5
ggtgagcaga gtgccctatc                                              20

SEQ ID NO: 6            moltype = DNA  length = 20
FEATURE                 Location/Qualifiers
source                  1..20
                        mol_type = other DNA
                        organism = synthetic construct
SEQUENCE: 6
gcagtctcca aacgcatgtc                                              20

SEQ ID NO: 7            moltype = DNA  length = 20
FEATURE                 Location/Qualifiers
source                  1..20
                        mol_type = other DNA
                        organism = synthetic construct
SEQUENCE: 7
tttgtgcacc agctgtctga                                              20
```

-continued

```
SEQ ID NO: 8           moltype = DNA  length = 20
FEATURE                Location/Qualifiers
source                 1..20
                       mol_type = other DNA
                       organism = synthetic construct
SEQUENCE: 8
ttgatcatgc catctccggc                                        20

SEQ ID NO: 9           moltype = DNA  length = 23
FEATURE                Location/Qualifiers
source                 1..23
                       mol_type = other DNA
                       organism = synthetic construct
SEQUENCE: 9
cagtagcagt aataggaagg cca                                    23

SEQ ID NO: 10          moltype = DNA  length = 20
FEATURE                Location/Qualifiers
source                 1..20
                       mol_type = other DNA
                       organism = synthetic construct
SEQUENCE: 10
aaggctccaa aagcaaagcc                                        20

SEQ ID NO: 11          moltype = DNA  length = 21
FEATURE                Location/Qualifiers
source                 1..21
                       mol_type = other DNA
                       organism = synthetic construct
SEQUENCE: 11
agggcagaat catcacgaag t                                      21

SEQ ID NO: 12          moltype = DNA  length = 20
FEATURE                Location/Qualifiers
source                 1..20
                       mol_type = other DNA
                       organism = synthetic construct
SEQUENCE: 12
agggtctcga ttggatggca                                        20

SEQ ID NO: 13          moltype = DNA  length = 21
FEATURE                Location/Qualifiers
source                 1..21
                       mol_type = other DNA
                       organism = synthetic construct
SEQUENCE: 13
gctcttcagt tcgtgtgtgg a                                      21

SEQ ID NO: 14          moltype = DNA  length = 21
FEATURE                Location/Qualifiers
source                 1..21
                       mol_type = other DNA
                       organism = synthetic construct
SEQUENCE: 14
gcctccttag atcacagctc c                                      21

SEQ ID NO: 15          moltype = DNA  length = 21
FEATURE                Location/Qualifiers
source                 1..21
                       mol_type = other DNA
                       organism = synthetic construct
SEQUENCE: 15
caattcctgg cgatacctca g                                      21

SEQ ID NO: 16          moltype = DNA  length = 21
FEATURE                Location/Qualifiers
source                 1..21
                       mol_type = other DNA
                       organism = synthetic construct
SEQUENCE: 16
gcacaactcc ggtgacatca a                                      21
```

METHOD FOR HAIR CARE BY USING CASHEW TESTA EXTRACT

CROSS-REFERENCE TO RELATED APPLICATION

This application claims the benefit of U.S. provisional application Ser. No. 63/503,503, filed on May 22, 2023. The entirety of the above-mentioned patent application is hereby incorporated by reference herein and made a part of the specification.

REFERENCE OF AN ELECTRONIC SEQUENCE LISTING

The contents of the electronic sequence listing (P234554USI.xml; Size: 14,985 bytes; and Date of Creation: May 21, 2024) is herein incorporated by reference in its entirety.

BACKGROUND

Technical Field

The present invention relates to the use of *Anacardium occidentale*, particularly to a method for hair care by using a cashew testa extract.

Related Art

Since an organic and/or natural dietary concept rises, biotechnology companies and food industry operators have actively invested in the research and development of relevant products about natural plants. To provide a scientifically validated basis for the benefits of plant-related products to physical health, the activity ingredient analysis and efficacy assessment of plants become a key project in product development.

*Anacardium occidentale*, also referred to as cashew nut, is a popular nut. *Anacardium occidentale* trees are originally derived in Northern Brazil, but now have been planted in many tropics and subtropics, for example Vietnam. *Anacardium occidentale* has rich nutritional values, and the *Anacardium occidentale* kernel contains rich unsaturated fatty acids, especially monounsaturated fatty acids, such as oleic acid. In addition, *Anacardium occidentale* also contains vitamin E, vitamin K, vitamin B6, calcium, magnesium, potassium, an antioxidant and other nutrient ingredients.

SUMMARY

In the field of hair care, people are increasingly paying attention to obtaining necessary nutrients from their diets to promote the health of scalps and hairs. Although there have been many care products in the market, and people are also increasingly aware of the influence of nutrients in their diets on hair, and relevant products in the market still have an improved space in the aspect of meeting consumer needs. Therefore, hair-related products attract attention and favor from consumers. Therefore, the inventors positively research and develop the use of *Anacardium occidentale* in hair-related products.

In some embodiments, provided is the use of a cashew testa extract for preparing a hair care composition. The cashew testa extract is prepared by extracting the testa of cashew nuts of *Anacardium occidentale* with a solvent.

In some embodiments, provided is a method for hair care, comprising administering to a subject in a need thereof a composition comprising a cashew testa extract.

In some embodiments, in the step of extraction, a solid-to-liquid ratio of the cashew testa to water is 5-20:1-5, the extraction temperature is 80° C.-90° C., and the extraction time is 80 min-120 min.

In some embodiments, the cashew testa extract has an ability of improving hair follicle health.

In some embodiments, the cashew testa extract increases hair follicle health by improving the antioxidant ability of hair follicle cells.

In some embodiments, the cashew testa extract increases hair follicle health by promoting the proliferation of hair follicle cells.

In some embodiments, the above cashew testa extract includes at least one compound selected from the group consisting of epicatechin coumaric acid ester, phloroglucinol, protocatechuic acid, and naringin 7-O-(6"-O-p-coumaryl)-β-D-glucoside.

In some embodiments, the cashew testa extract improves hair follicle health by promoting hair follicle angiogenesis.

In some embodiments, the cashew testa extract improves hair follicle health by promoting the expression of germinal genes.

In some embodiments, the cashew testa extract improves hair follicle health by reducing the expression of hair loss genes.

In some embodiments, the cashew testa extract improves hair follicle health by reducing the concentration of MDA in blood.

In some embodiments, the cashew testa extract has an ability of increasing a hair diameter.

In conclusion, the cashew testa extract can be used for preparing a hair care composition according to any one of the embodiments. In some embodiments, provided is a method for hair care, comprising administering to a subject in need thereof a composition comprising a cashew testa extract. In some embodiments, when being administered to an individual, the prepared hair care composition can generate the effect of improving or promoting hair health of the individual, that is to say, the above hair care composition has the function of hair care. In some embodiments, the cashew testa extract also has the following one or more abilities: improving the antioxidant ability of hair follicle cells, promoting hair follicle angiogenesis, promoting the expression of germinal genes, reducing the expression of hair loss genes, and increasing the diameter of the hair.

DETAILED DESCRIPTION

Figure 1:
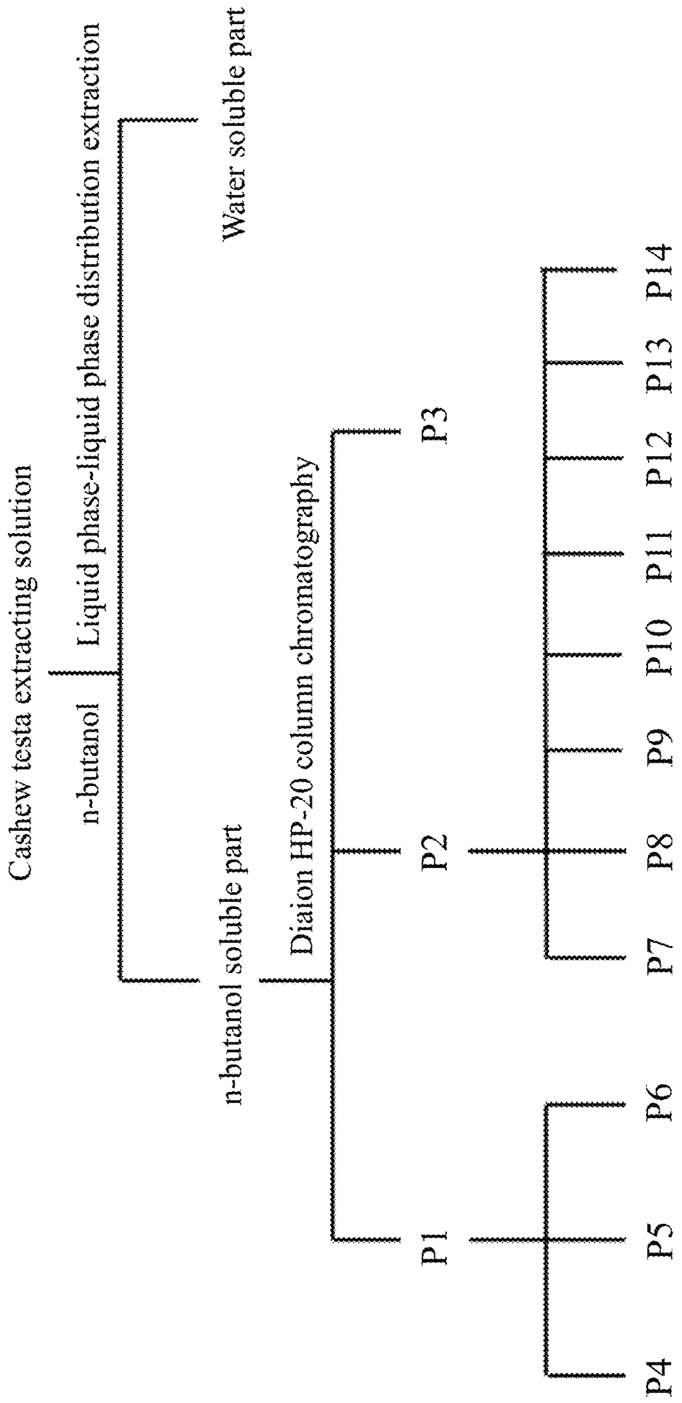
FIG. 1 is a flowchart showing the separation of compounds from a cashew testa extract.

Next, some embodiments of the present invention will be described in detail. The present invention can be practiced in multiple different forms without deviating from the spirit of the present invention, and the scope of protection should not be limited to specific conditions stated in specification.

In some embodiments, the cashew testa extract is obtained by extracting the testa of cashew nut of *Anacardium occidentale.*

In some embodiments, the testa of cashew nut of *Anacardium occidentale* subjected to extraction is a kernel membrane of *Anacardium occidentale* (also referred to as an *Anacardium occidentale* seed coat, or an *Anacardium occidentale* peel). The testa of cashew nut of *Anacardium occidentale* is one of an inner membrane, a membrane-like substance, an outer skin or a seed shell of *Anacardium occidentale*, or a combination thereof, all of which are later referred to as the cashew testa.

In some embodiments, during the extraction, the cashew testa subjected to extraction can be a raw material (for example, a complete cashew testa), or can be decomposed into small-sized shapes through physical pretreatment, such as debris, particles or powders. The adopted physical pretreatment can include at least one of crude smashing, chopping, cutting, stamping and grinding.

In some embodiments, the solvent can be water, alcohols, or a combination thereof. During the extraction, the cashew testa is extracted with the solvent at 80° C.-90° C. for 80 min-120 min to obtain an initial extracting solution. For example, the cashew testa can be soaked into water at 85±5° C. for 90 min, so that the effective ingredients of the cashew testa are dissolved into the solvent so as to obtain the initial extracting solution.

In some embodiments, during the extraction, a weight ratio of the cashew testa to the solvent is 5-20:1-5. For example, a weight ratio of the cashew testa to water is 10:1.

In some embodiments, during the extraction, the initial extracting solution can be further filtered to remove solids such as the cashew testa after extraction with the solvent so as to obtain a cashew testa filtrate. For example, the initial extracting solution is filtered by using a 400-mesh filter screen to remove fine solids. Afterwards, the filtered cashew testa filtrate is subjected to vacuum concentration at 60° C.±5° C. under the steam of 1±0.2 kg/cm$^2$ until the Degrees Brix of the solution is 8.8±0.5, at this moment, the concentration is ended, so as to obtain a cashew testa concentrate. Where, if the pH of the obtained cashew testa concentrate is higher than 4.0, 0.23% malic acid can be added so that the pH of the cashew testa concentrate is reduced to 3.2±0.5, so as to obtain the cashew testa extracting solution.

In some embodiments, the cashew testa extract can be at least one of the initial extracting solution, the cashew testa filtrate, the cashew testa concentrate or the cashew testa extracting solution adjusted with malic acid, or a combination thereof.

In some embodiments, the cashew testa extract can reduce the concentration of malondialdehyde (MDA) in organism blood. The concentration of MDA in organism blood is a product obtained by peroxidation of cellular lipids after receiving attacks from free radicals; the more MDA accumulation in the body represents the poorer antioxidant ability of the body. Specifically, the cashew testa extract can reduce the concentration of MDA in blood and then the antioxidant ability in the body is promoted, and therefore the cashew testa extract is suitable for preparation of an organism composition having antioxidant properties.

In some embodiments, provided is a method for hair care, comprising administering a subject in a need thereof a composition comprising a cashew testa extract.

In some embodiments, the above organism can be human.

In some embodiments, the cashew testa extract can reduce the ROS (reactive oxygen species) in the organism to reduce hair follicle cell damage. The appropriate ROS level is necessary for normal functions of cells, however, excessive ROS can cause oxidative stress on hair follicle cells, which leads to cell damage and apoptosis and affects the normal function of hair follicles, so as to affect hair growth cycle and health. Thus, the cashew testa extract is suitable for preparing a combination capable of reducing hair follicle cell damage.

In some embodiments, a method for reducing hair follicle cell damage, comprising administering a subject in a need thereof a combination comprising a cashew testa extract.

In some embodiments, those skilled in the art can elicit some correlated conclusions by virtue of data analysis on reduction in organism ROS through the concentration of MDA in the organism blood: the cashew testa extract promotes the antioxidant ability of the organism, and the cashew testa extract promotes the antioxidant ability of the hair follicle cells. In other words, the cashew testa extract can be used for preparing a hair care composition capable of promoting the antioxidant ability of the hair follicle cells.

In some embodiments, a method for promoting the antioxidant ability of the hair follicle cells, comprising administering a subject in a need thereof a composition comprising a cashew testa extract.

In some embodiments, the cashew testa extract has the function of promoting hair follicle health. The promoting hair follicle health can be achieved by reducing hair follicle cell damage, increasing the proliferation of hair follicle cells, or a combination thereof. Where, the cashew testa extract includes compounds obtained after the cashew testa extract is separated, which comprises at least one compound of epicatechin coumaric acid ester, phloroglucinol, protocatechuic acid, and naringenin 7-O-(6"-O-p-coumaryl)-β-D-glucoside, or a combination thereof.

In some embodiments, the compound of the cashew testa extract is gallic acid, gallocatechin, epicatechin gallate, epicatechin coumarin ester, phloroglucinol, protocatechuic acid, or naringenin 7-O-(6"-O-p-coumaryl)-β-D-glucoside.

Reasons for affecting hair loss include intrinsic and extrinsic factors. The extrinsic factors include lifestyle factors such as stress, irregular lifestyle habits, drug effects, diseases such as thyroid problems, as well as dietary and environmental factors such as nutritional imbalances or insufficient intake, and even hair styling behaviors such as perming and dyeing, which can also cause hair problems. The intrinsic factors mainly include effects of genetic genes and dihydrotestosterone (DHT), and local microcirculation issues. The genetic genes make scalp hair follicle more sensitive to hormone, and DHT may cause hair loss for partial hair follicles. Meanwhile, poor blood circulation may also lead to hair loss due to insufficient nutrition. In some embodiments, the cashew testa extract has the function of promoting hair follicle health to improve the intrinsic factors of hair loss. For example, the promotion of the hair follicle health is one of reduction in hair follicle cell damage, increase in hair follicle cell proliferation, increase in hair follicle angiogenesis, improvement in expression of germinal genes or reduction in expression of hair loss genes. Therefore, the cashew testa extract is suitable for preparing a hair care composition.

In some embodiments, the cashew testa extract can effectively increase the expression of hair follicle cell angiogenesis genes, and the angiogenesis genes can be VEGF genes (vascular endothelial growth factors). A protein encoded by the vascular endothelial growth factors can bind to a VEGF receptor (VEGFR) on the surface of endothelial cells in blood vessels so as to initiate various signaling pathways such as intracellular tyrosine kinase, including but not limited to a PI3K Akt pathway, a Ras-Raf-MEK-ERK pathway and a Src kinase pathway, thereby promoting the process of angiogenesis and then achieving the effect of promoting the transportation of germinal nutrients. Specifically, the health and vitality of hair follicle cells are closely related to the supply of peripheral blood vessels, and the expression of angiogenesis genes is related to the formation and proliferation of blood vessels. The cashew testa extract has the ability of increasing the expression of VEGF genes by about 1.26 times, so as to increase the expression of angiogenesis-related genes in hair follicle cells, promote the proliferation and development of peripheral blood vessels and improve the transporting ability of blood vessels on nutrients, so that the hair follicle cells obtain more nutrients to promote the growth and health of hairs. Therefore, the cashew testa extract is suitable for preparing a hair care composition capable of promoting hair follicle angiogenesis.

In some embodiments, a method for hair care to increase hair follicle angiogenesis, comprising administering a subject in a need thereof a composition comprising a cashew testa extract.

In some embodiments, the cashew testa extract can effectively increase the expression of angiogenesis genes of hair follicle cells, and the angiogenesis genes can be IGF-1 genes. A protein encoded by IGF-1 genes can bind to a receptor (IGF-1R (Insulin-like Growth Factor 1 Receptor) or IR (Insulin Receptor)) on the surface of endothelial cells in blood vessels so as to initiate various signaling pathways such as intracellular tyrosine kinase, including but not limited to a PI3K Akt pathway, a Ras-Raf-MEK-ERK pathway and a Src kinase pathway, thereby promoting the process of angiogenesis and then achieving the effect of promoting the transportation of germinal nutrients. Specifically, the health and vitality of hair follicle cells are closely related to the supply of peripheral blood vessels, and the expression of angiogenesis genes is related to vasodilation and vascular resistance. The cashew testa extract has the ability of increasing the expression of IGF-1 genes by about 1.5 times, so as to increase the expression of angiogenesis-related genes in hair follicle cells, promote peripheral vasodilation, reduce vascular resistance and improve the transporting ability of blood vessels on nutrients, so that hair follicle cells obtain more nutrients to promote the growth and health of hairs. Therefore, the cashew testa extract is suitable for preparing a hair care composition capable of promoting hair follicle angiogenesis.

In some embodiments, the cashew testa extract can effectively promote the expression of germinal genes, and the germinal genes can be XROX20 genes. A protein encoded by XROX20 genes regulates and controls the development processes of hair follicles, including but not limited to adjustment of hair cycle, control of hair pigment generation and promotion of hair follicle formation. The cashew testa extract has the ability of increasing the expression of XROX20 genes by about 1.93 times, so as to increase the expression of germinal related genes in hair follicle cells. Therefore, the cashew testa extract is suitable for preparing a hair care composition capable of promoting expression of germinal genes.

In some embodiments, the cashew testa extract can effectively promote the expression of germinal genes, and the germinal genes can be SCF genes. A protein encoded by SCF genes is a cell factor, referred to as a hematopoietic stem cell factor (called SCF for short). SCF plays important physiological roles in many tissues and organs, including regulation and control of hair growth and hair follicle functions. The cashew testa extract has the ability of increasing the expression of SCF genes by about 1.08 times, so as to improve the expression of germinal related genes in hair follicle cells. Therefore, the cashew testa extract is suitable for preparing a hair care composition capable of promoting expression of germinal genes.

In some embodiments, a hair care method for promoting expression of germinal genes, comprising a subject in a need thereof a composition comprising a cashew testa extract.

In some embodiments, the cashew testa extract can effectively inhibit the expression of hair loss genes, and the hair loss gene can be SRD5α1, SRD5α2, or a combination thereof. 5α-reductases encoded by 5α-SRD5α1 genes and SRD5α2 genes participate in the metabolic process of androgens, including: converting testosterone into more active dihydrotestosterone; excessive dihydrotestosterone is related to androgen-related intrinsic factors (for example male hair loss), the influence of dihydrotestosterone on hair follicles may lead to apoptosis and shortened growth cycles of hairs, thereby inhibiting hair follicle growth and also promoting sebaceous gland to secret oils and fats to result in hair loss and scalp oil production. The cashew testa extract has the abilities of inhibiting SRD5α1 genes by about 0.75 times and inhibiting SRD5α2 genes by about 0.68 times, so as to reduce the expression of hair loss genes to increase hair follicle health. Therefore, the cashew testa extract is suitable for preparing a hair care composition capable of reducing hair loss genes. In some embodiments, the cashew testa extract can effectively inhibit the expression of hair loss genes, and the hair loss genes can be AR (androgen receptor) genes. After binding to excessive dihydrotestosterone, the high-activity AR may aggravate the influence of androgen on hair follicles, leading to inhibition of hair growth from hair follicles so as to inhibit hair growth from hair follicles. The cashew testa extract has the ability of inhibiting AR genes by about 0.8 times, so as to reduce the expression of hair loss genes to increase hair follicle health. Therefore, the cashew testa extract is suitable for preparing a hair care composition capable of reducing hair loss genes.

In some embodiments, the cashew testa extract can effectively inhibit the expression of hair loss genes, and the hair loss genes can be TGF-β genes (encoding transformation growth factor-β). The TGF-β gene can inhibit the growth of hairs, promote inflammation and case hair loss and scalp inflammation under certain conditions. The certain conditions may be, but are not limited to change in androgen levels. The cashew testa extract has the ability of inhibiting TGFβ genes by about 0.87 times, so as to reduce hair loss genes to increase hair follicle health. Therefore, the cashew testa extract is suitable for preparing a hair care composition capable of reducing hair loss genes.

In some embodiments, a hair care method for reducing hair loss genes, comprising administering a subject in a need thereof a composition comprising a cashew testa extract.

In some embodiments, the cashew testa extract is used for preparing a composition for hair health. For example, the composition can be a capsule containing cashew testa extract powders, or a beverage containing a liquid cashew testa extract. In some embodiments, a composition comprises a container and a cashew testa extract in the container. For example, the cashew testa extract beverage is *Anacardium occidentale* beverage containing the cashew testa extract in the container.

In some embodiments, a hair care method for reducing hair loss genes, comprising administering a subject in a need thereof a composition comprising a cashew testa extract.

In some embodiments, the above composition can be prepared into dosage forms suitable for transintestinal, parenteral or oral administration, by utilizing techniques that are well known to those skilled in the art.

In some embodiments, the transintestinal or oral dosage form can be, but is not limited to, a tablet, a troche, a lozenge, a pill, a capsule, dispersible powder, a granule, a solution, a suspension, an emulsion, a syrup, an elixir, a slurry, or an analogue thereof.

In some embodiments, when the above composition is an edible composition, the edible composition comprises a specific amount of cashew testa extracts. Where, the dosage form of the edible composition can be powder, granule, solution, colloid or ointment.

In some embodiments, the edible composition containing the cashew testa extract can be a food product or a food additive.

In some embodiments, the edible composition containing the cashew testa extract can be beverages, fermented foods, bakery products, health foods, dietary supplements, or the like. In some embodiments, the edible composition containing the cashew testa extract can further comprise an adjuvant. For example, the adjuvant can be maltodextrin, malic acid, sucralose, citric acid, fruit spice, honey spice, steviol glycosides, or a combination thereof. The types and quantity of the selected adjuvant are included within the scope of protection of those skilled in the art.

In some embodiments, the food additive can be a seasoning, a sweetener, spice, a pH adjuster, an emulsifier, a colorant or a stabilizer.

In some embodiments, in the above composition, the daily intake of the cashew testa extract is 4 g of liquid.

In the following examples, unless otherwise specified, experimental steps are carried out at room temperature (25° C.-30° C.) and under normal pressure (1 atm). Furthermore, statistical analysis is performed by using Excel software in the following examples. Data is expressed as mean±standard deviation (SD), and the difference between groups is expressed as student's t-test. In the figures, "*" represents that p is less than 0.05, "" represents that p is less than 0.01, and "*" represents that p is less than 0.001. The more "*" represents more obvious statistical differences.

Example 1: Preparation of Cashew Testa Extract

A. Materials:

1. Cashew testa (place of origin: Vietnamese)
2. Secondary water, also referred to as RO water (reverse osmosis) or secondary distilled water, hereinafter referred to as "water".

B. Preparation Procedure:

1. Water was heated to 85±5° C., and then cashew testa was added and soaked into water at 85±5° C. for 90 min to form an initial extracting solution containing a solid. Therefore, a weight ratio of the added cashew testa to water was 1:10.
2. The cooled initial extracting solution was filtered with a 400-mesh filter screen to remove the solid (i.e., the extracted cashew testa), so as to obtain a cashew testa filtrate.
3. Vacuum concentration was performed on the filtrate by using a concentration machine after the temperature of the concentration machine (mode: Rotavapor R-100; brand: BUCHI) was set as 60±5° C. The concentration was stopped when the Degree Brix of the filtrate was concentrated to 8.8±0.5° Bx, so as to obtain a cashew testa concentrate.
4. 0.23% malic acid was added into the cashew testa concentrate so that the pH of the cashew testa concentrate was adjusted to pH 3.2±0.5, and then a cashew testa extracting solution was obtained.

Example 2: Compound Analysis Test

A. Materials and Instruments:

1. Nuclear Magnetic Resonance Spectrometer (NMR): 1D and 2D spectra use Ascend 400 MHz, which is purchased from Bruker Co., Germany, δ represents chemical shift, and the unit is ppm.
2. High resolution liquid chromatography mass spectrometer: connected with ultra-performance liquid chromatography (Ultimate 3000 HPLC, which is purchased from Thermo Fisher Scientific) and high-resolution orbital ion well mass spectrometer (Q-EXACTIVE System with Ion Max Source, which is purchased from Thermo Fisher Scientific) in series for measurement, and the unit is m/z.
3. Medium pressure liquid chromatography (MPLC): CombiFlash® Rf+, which is purchased from Teledyne ISCO, Lincoln, Nebraska, USA.
4. High Performance Liquid Chromatography (HPLC): High Performance Liquid Chromatography (HPLC) is a Hitachi Chromaster 5260 series; Hitachi Chromaster 5110 for solvent extraction and transportation system; Hitachi Chromaster 5310, a constant temperature device for columns; the Diode Array Detector (DAD) is Hitachi chrome 5430 with a detection wavelength of 280 nm.
5. HPLC analysis column: Mightysil RP-18 GP 250 (250×4.6 mm, 5 μm, which is purchased from Kanto, Tokyo, Japan).

6. Column Chromatography Filling Materials:

(1) Macroporous resin: Diaion HP-20, which is purchased from Mitsubishi Chemical Company, Japan.

(2) Normal phase silica gel: Merck Kieselgel 60, 40-63 μm, which is purchased from Merck, Germany, with product number Art.9385.

(3) Reverse phase silica gel: Merck LiChroprep® RP-18, 40-63 μm, which is purchased from Merck, Germany, with product number Art.0250.

7. Thin-Layer Chromatography:

(1) Normal phase TLC aluminum sheet: thin-Layer Chromatography sheet coated with silica gel 60 $F_{254}$ (0.25 mm), which is purchased from Merck, Germany.

(2) Reverse phase TLC aluminum sheet: thin-Layer Chromatography sheet coated with silica gel RP-18 $F_{254-S}$ (0.25 mm), which is purchased from Merck, Germany.

8. UV Lamp: UVP UVGL-25, with the wavelengths of 254 nm and 365 nm.

9. Solvent: methanol, n-butanol, methanol-d4 (a deuterization degree of 99.5%), deuterium oxide (a deuterization degree of >99.8%) and dimethyl sulfoxide-d6 (a deuterization degree of >99.9%), which are all purchased from Merck, Taiwan.

10. Filter membrane: a polyvinylidene fluoride membrane filter (PVDF) with a pore size of 0.22 μm, which is purchased from Millipore, USA.

11. Sample: A Cashew Testa Extract Obtained in Example 1

B. Compound Separation and Structure Identification Procedure:

1. Liquid phase-liquid phase distribution extraction was performed on 5 L of cashew testa extract obtained in example 1 based on n-butanol as a solvent to obtain 48.9 g of n-butanol soluble part (lipid-soluble component) and 156.3 g of water soluble part (water-soluble component), so as to separate the lipid-soluble component of the cashew testa extract obtained in example 1 from the water-soluble component of the cashew testa extract obtained in example 1, and the separation and purification process adopted a bioassay guided fractionation.

2. 40 g of n-butanol soluble part obtained in step 1 was continued to be subjected to initial separation by using a Diaion HP-20 macroporous resin column chromatography separation method, 3 separation parts (hereinafter referred to as a first separation part P1, a second separation part P2 and a third separation part P3) were obtained by respectively using 5 L of pure water, 5 L of pure water-methanol (a volume ratio of 1:1) and 5 L of methanol as extracting solutions.

3. The first separation part P1 was taken and separated again by reverse phase-medium pressure liquid chromatography (RP-MPLC) to obtain multiple extracts. Therefore, the extracting solutions from water to methanol were used for extraction, the extraction time was 60 min, and the flow rate was 15 ml/min. The extracts with similar results were combined by using reverse phase thin-layer chromatography (reverse phase TLC aluminum sheet: thin-layer chromatography sheet coated with RP-18 $F_{254-S}$ (0.25 mm)), so as to obtain 3 secondary separation parts, as shown in FIG. 1 (hereinafter referred to as a fourth separation part P4, a fifth separation part P5 and a sixth separation part P6).

Figure 2:
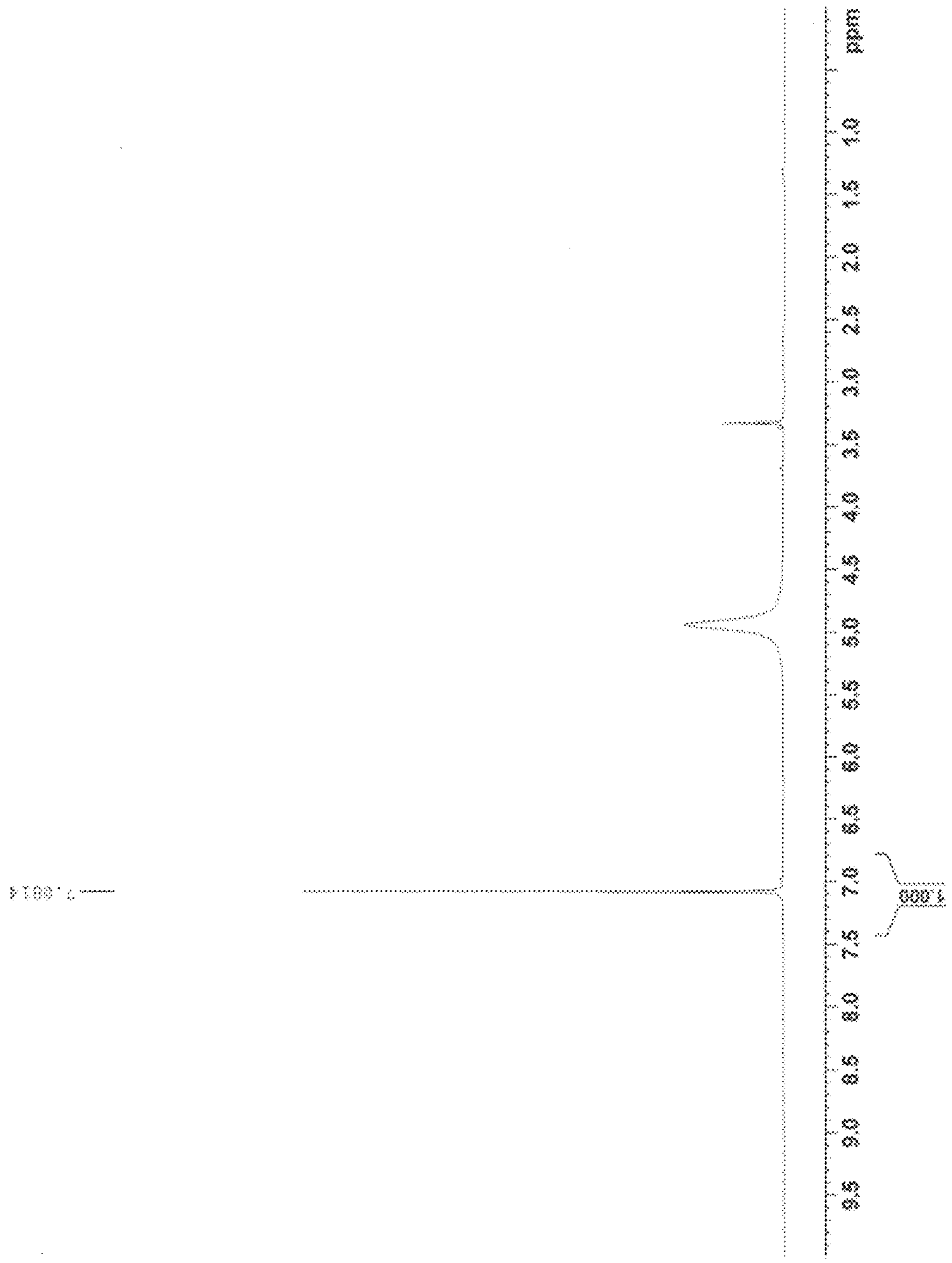
FIG. 2 is a proton-nuclear magnetic resonance spectroscopy ($^1H$ NMR) image of gallic acid.

4. The fifth separation part P5 was purified by reverse phase-high efficiency liquid chromatography (methanol/water=1/19) to obtain a compound TCI-CsN-01. After the chemical structure was analyzed by hydrogen-nuclear magnetic resonance spectroscopy ($^1$H-NMR), and the compound TCI-CsN-01 was identified as gallic acid, as shown in FIG. 2.

Figure 6:
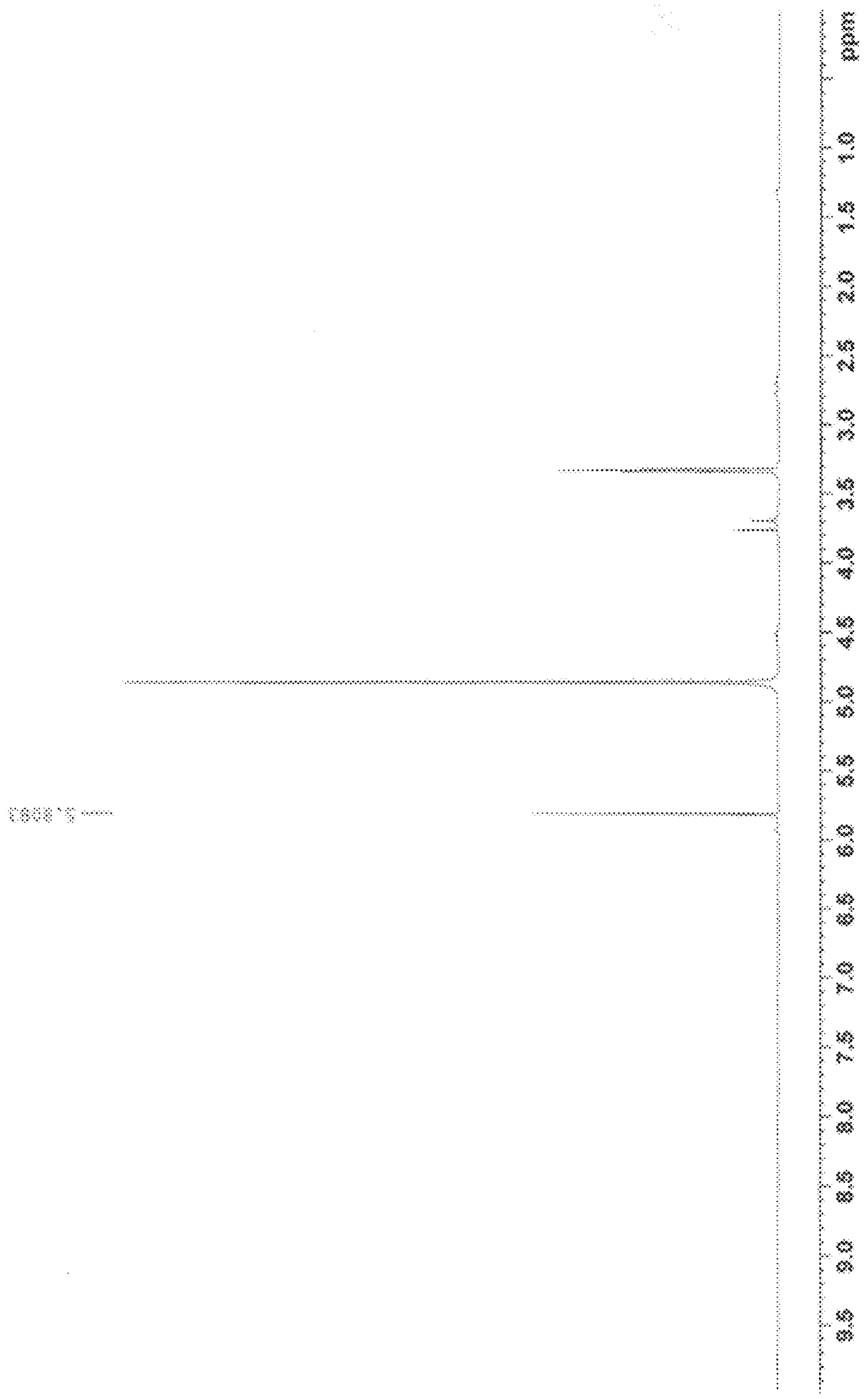
FIG. 6 is a ($^1H$ NMR) image of phloroglucinol.
Figure 7:
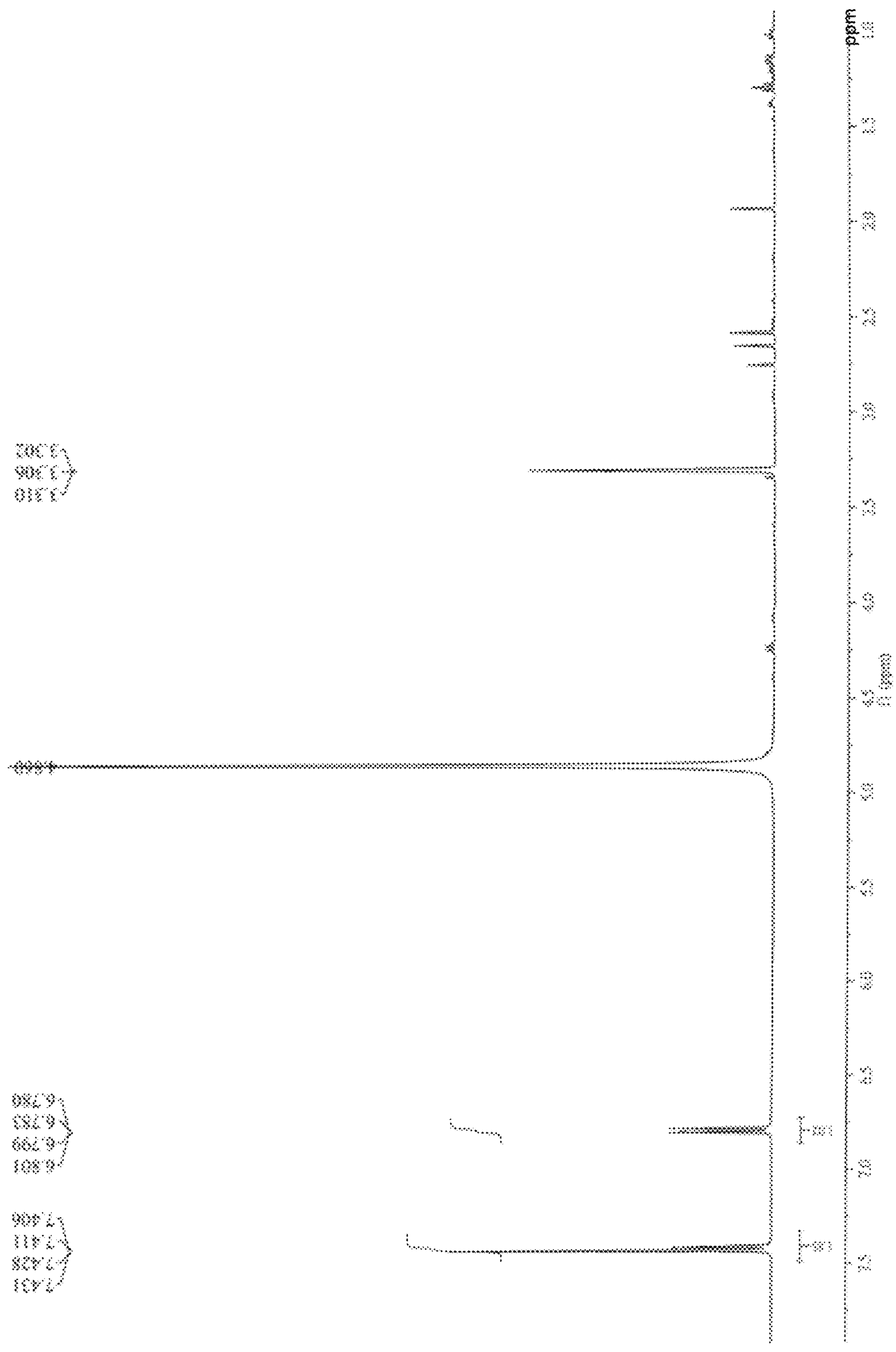
FIG. 7 is a ($^1H$ NMR) image of protocatechuic acid.

5. The sixth separation part P6 was purified by reverse phase-high efficiency liquid chromatography (methanol/water=1/9) to obtain compounds TCI-CsN-11 and TCI-CsN-12. The compound TCI-CsN-11 was identified as phloroglucinol, and TCI-CsN-12 was identified as protocatechuic acid, as shown in FIG. 6 and FIG. 7.

6. The second separation part P2 was taken and separated again by reverse phase-medium pressure liquid chromatography (RP-MPLC) to obtain multiple extracts. Therefore, the extracting solutions from water to methanol were used for extraction, the extraction time was 100 min, and the flow rate was 15 ml/min. The extracts with similar results were combined by using reverse phase thin-layer chromatography so as to obtain 8 secondary separation parts, as shown in FIG. 1 (hereinafter referred to as a seventh separation part P7, an eighth separation part P8, a ninth separation part P9, a tenth separation part P10, an eleventh separation P11, a twelve separation part P12, a thirteenth separation part P13 and a fourteenth separation P14).

Figure 3:
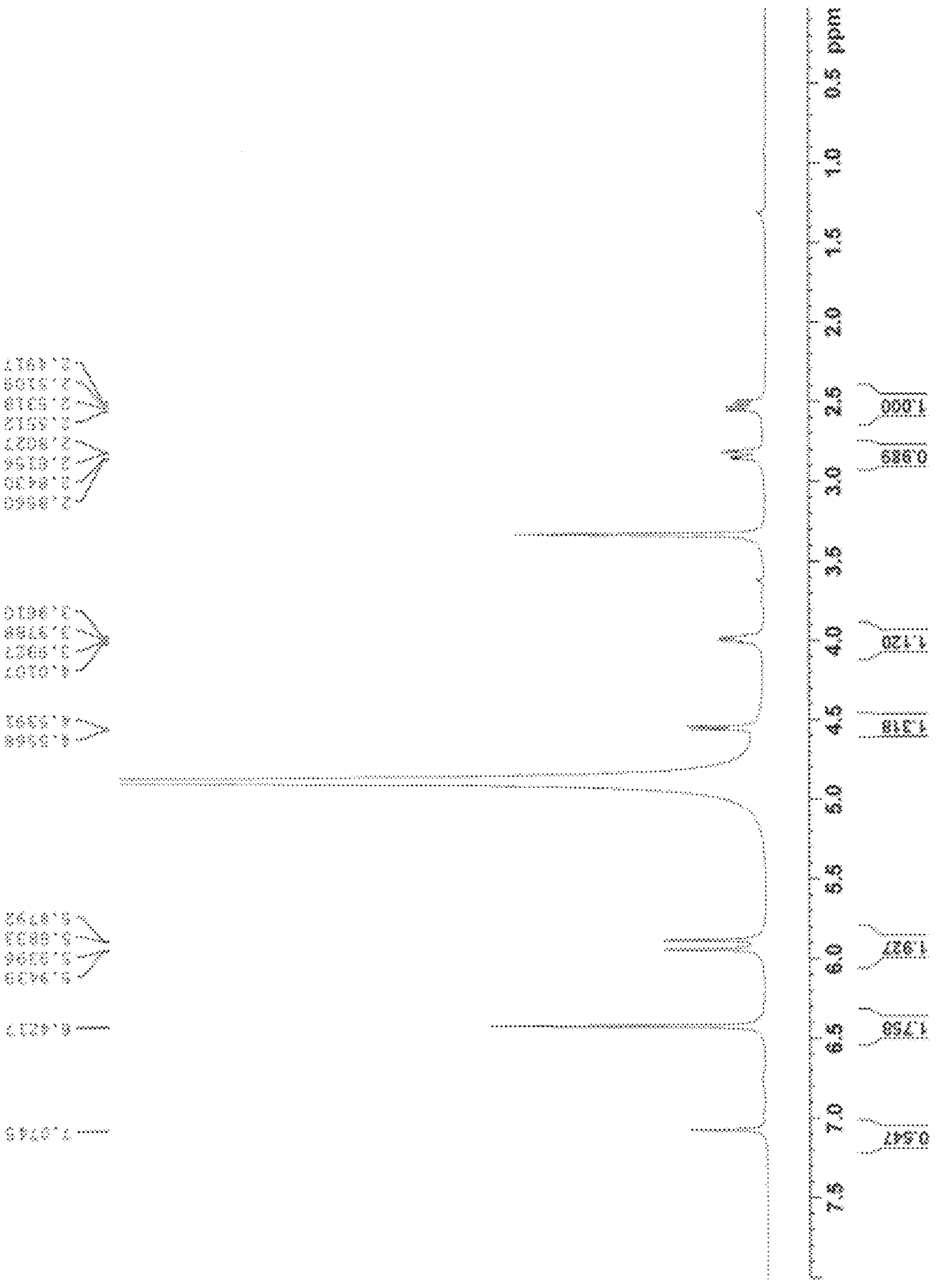
FIG. 3 is a ($^1H$ NMR) image of gallocatechin.

7. The seventh separation part P7 was purified by reverse phase-HPLC (methanol/water=3/17) to obtain a compound TCI-CsN-02. After the chemical structure was analyzed by hydrogen-nuclear magnetic resonance spectroscopy ($^1$H-NMR), the compound TCI-CsN-02 was identified as gallocatechin, as shown in FIG. 3.

Figure 4:
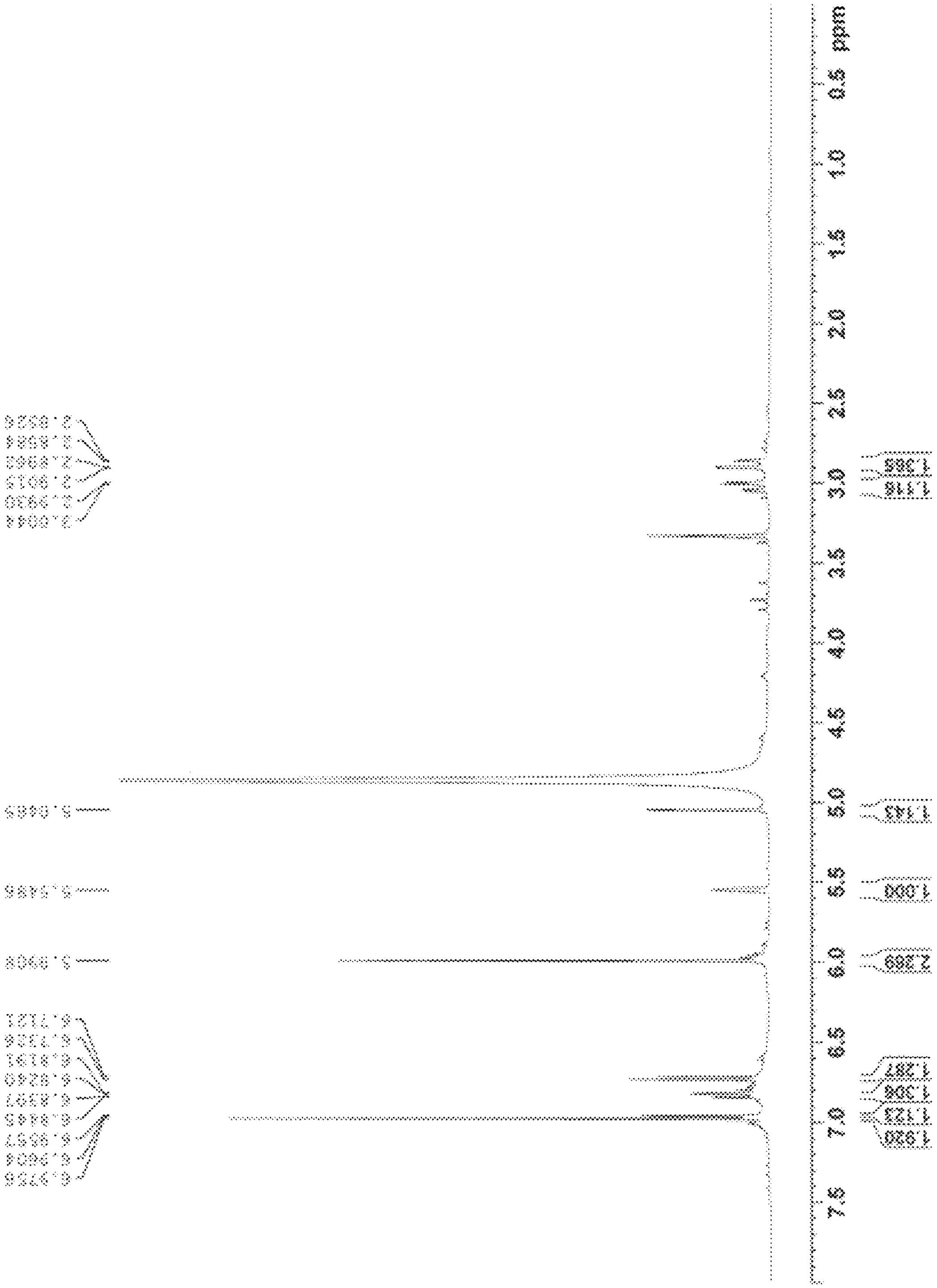
FIG. 4 is a ($^1H$ NMR) image of epicatechin gallate.

8. The tenth separation part P10 was purified by reverse phase-HPLC (methanol/water-3/7) to obtain a compound TCI-CsN-07. TCI-CsN-07 was identified as epicatechin gallate, as shown in FIG. 4.

Figure 8:
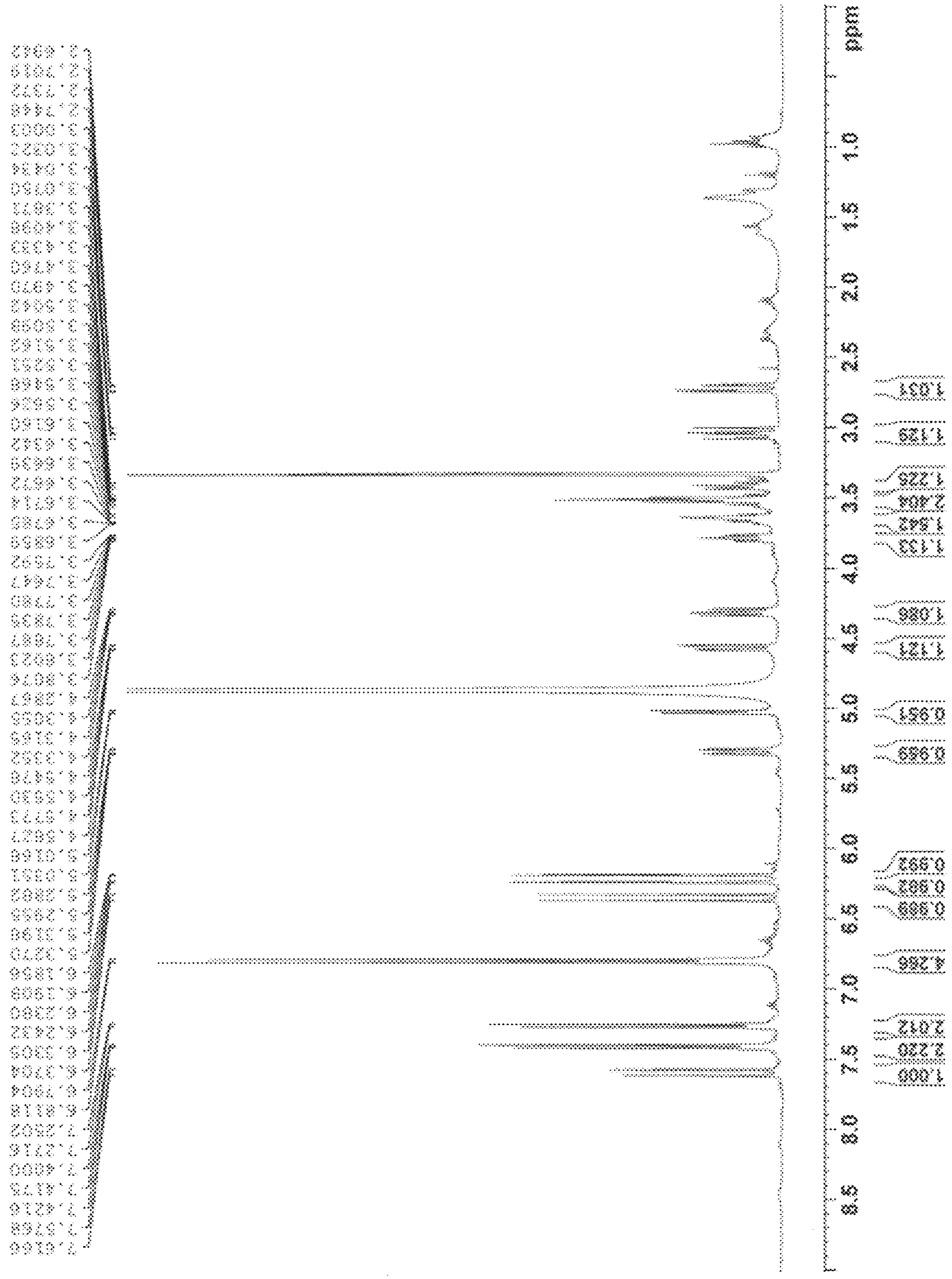
FIG. 8 is a ($^1H$ NMR) image of naringenin 7-O-(6"-O-p-coumaryl)-β-D-glucoside.

9. The eleventh separation part P11 was purified by reverse phase-HPLC (methanol/water-2/3) to obtain a compound TCI-CsN-13. TCI-CsN-13 was identified as naringenin 7-O-(6"-O-p-coumaryl)-β-D-glucoside, as shown in FIG. 8.

Figure 5:
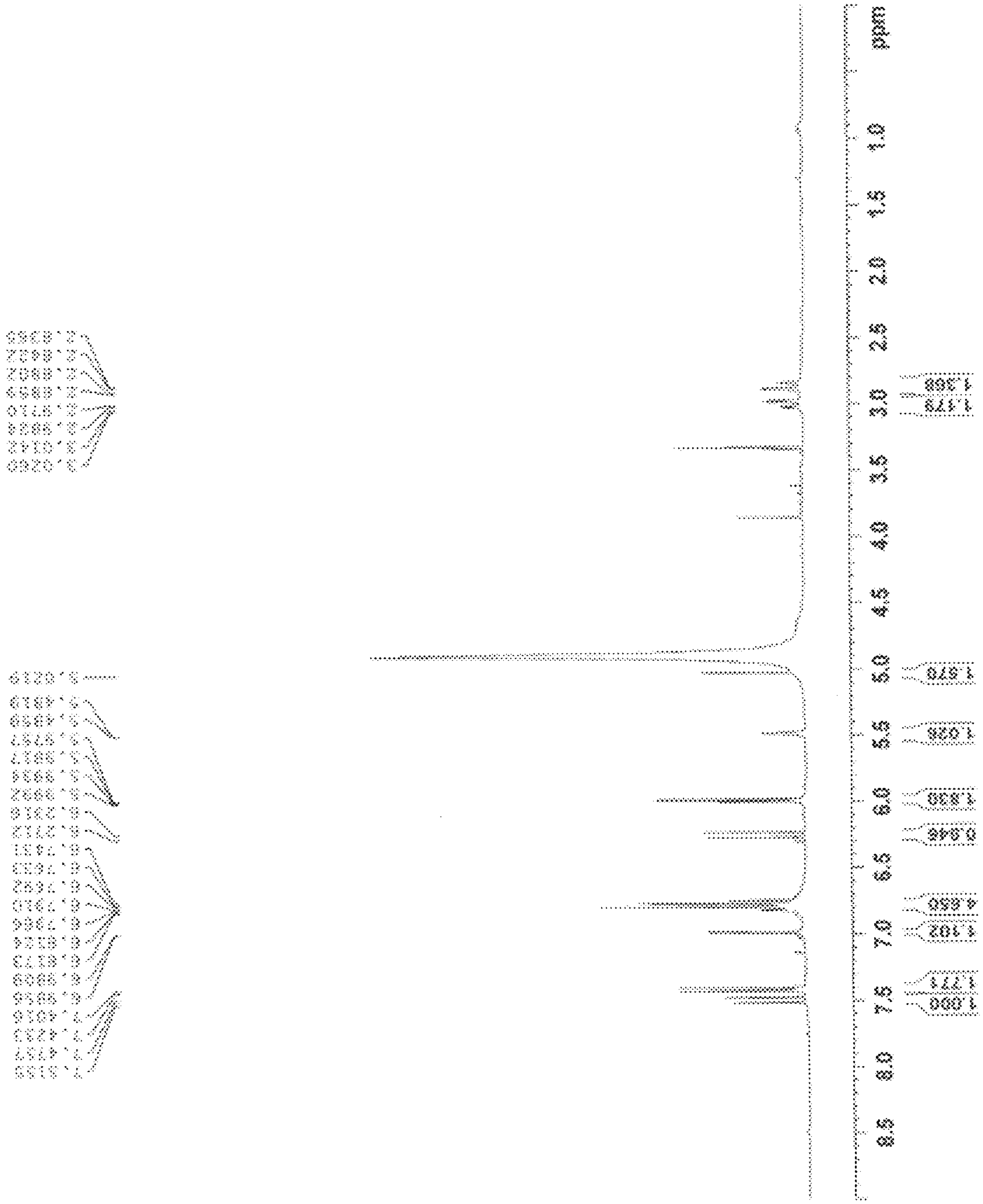
FIG. 5 is a ($^1H$ NMR) image of epicatechin coumarin ester.

10. The thirteenth separation part P13 was purified by reverse phase-HPLC (methanol/water=1/1) to obtain a compound TCI-CsN-05. After the chemical structure was analyzed by proton-nuclear magnetic resonance spectroscopy ($^1$H-NMR), the compound TCI-CsN-05 was identified as epicatechin coumarate through literature comparison, as shown in FIG. 5.

The names and chemical structure formulas of the above compounds are as shown in Table 1 below.

TABLE 1

| Compound number | Compound name | IUPAC nomenclature | Chemical structural formula |
|---|---|---|---|
| TCI-CsN-01 | Gallic acid | 3,4,5-trihydroxybenzoic acid | 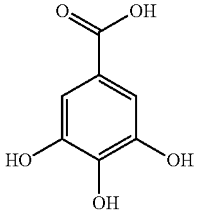 |

TABLE 1-continued

| Compound number | Compound name | IUPAC nomenclature | Chemical structural formula |
|---|---|---|---|
| TCI-CsN-02 | Gallocatechin | (2R,3S)-2-(3,4,5-trihydroxyphenyl)-3,4-dihydro-2H-chromose-3,5,7-triol | 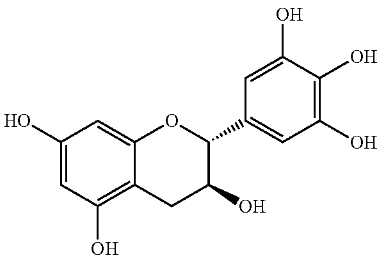 [SMILES: Oc1cc(O)c2c(c1)O[C@H](c1cc(O)c(O)c(O)c1)[C@@H](O)C2] |
| TCI-CsN-05 | Epicatechin coumarin ester | (2R,3R)-2-(3,4-trihydroxyphenyl)-3,4-dihydro-2H-chromose-3,5,7-triol | 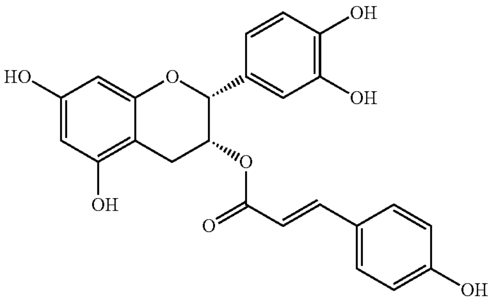 [SMILES: O=C(/C=C/c1ccc(O)cc1)O[C@@H]1Cc2c(O)cc(O)cc2O[C@@H]1c1ccc(O)c(O)c1] |
| TCI-CsN-07 | Epicatechin gallate | [(2R,3R)-2-(3,4-dihydroxyphenyl)-5,7-dihydroxy-3,4-dihydro-2H-benzopyran-3-yl]3,4,5-trihydroxybenzoate | 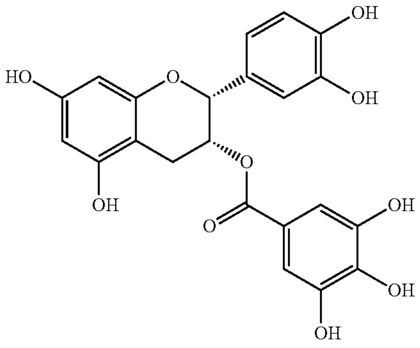 [SMILES: O=C(O[C@@H]1Cc2c(O)cc(O)cc2O[C@@H]1c1ccc(O)c(O)c1)c1cc(O)c(O)c(O)c1] |
| TCI-CsN-11 | Phloroglucinol | 1,3,5-benzenetriol | 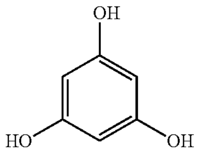 |
| TCI-CsN-12 | Protocatechuic acid | 3,4-dihydroxybenzoic acid | 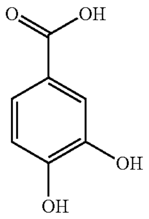 [SMILES: O=C(O)c1ccc(O)c(O)c1] |
| TCI-CsN-13 | Naringenin 7-O-(6"-O-p-coumaryl)-β-D-glucoside | 5-hydroxy-2-(4-hydroxyphenyl)-7-[(2S,3R,4S,5S,6R)-3,4,5-trihydroxy-6-(hydroxymethyl)oxycyclohexane-2-yl]oxo-2,3-dihydrochromen-4-one | 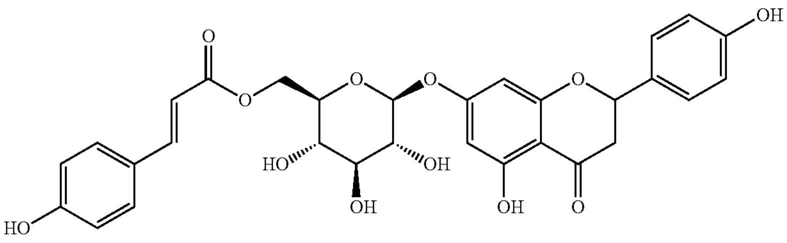 [SMILES: O=C(/C=C/c1ccc(O)cc1)OC[C@H]1O[C@@H](Oc2cc(O)c3c(c2)OC(c2ccc(O)cc2)CC3=O)[C@H](O)[C@@H](O)[C@@H]1O] |

Example 3: Antioxidant Test for Hair Follicle Cells

A. Materials and instruments:

1. Cell strains: human hair follicle dermal papilla cells (HFDPC), which are purchased from PromoCell, with a cell number C-12071, and hereinafter referred to as HFDPC cells.

2. Cell culture medium: follicle dermal papilla cell growth medium (purchased from PromoCell, with a product number C-26501).

3. DCFH-DA treatment reagent: which is prepared from DCFH-DA (2'7'-dichlorodioxine diacetate) (purchased from Sigma, with a product number SI-D6883-50 MG) and DMSO (purchased from Sigma, with a product number 472301).

4. 1×DPBS preparation: 10×DPBS was diluted by 10 times with sterilized $ddH_2O$.

5. 100 mM $H_2O_2$ aqueous solution: $H_2O_2$ and 1×DPBS were uniformly mixed in a volume ratio of 1:88 for later use.

6. Trypsin: which is prepared by diluting 10× trypsin (purchased from Gibco, with a product number 15400-054) with DPBS whose volume is 9 times that of 10× trypsin.

7. Flow cytometer with a model of BD Accuri, which is purchased from BD company.

B. Test Procedure:

1. HFDPC cells were inoculated into a 6-well culture medium with 2 ml of cell culture medium in each well at the density of $1\times10^5$ cells, and cultured at 37° C. for 24 h. Therefore, the HFDPC cells were divided into three test groups which were blank group G01, control group G02 and experimental group, respectively.

2. After culture for 24 h, each group was changed as an experimental culture medium. Where, the experimental culture media in blank G01 and control group G02 were cell culture mediums without cashew testa extracts or compounds thereof. The experimental culture medium in experimental group is as shown in Table 2 and Table 3. Subsequently, each group was treated at 34° C. for 1 h.

TABLE 2

| Group | Experimental culture medium |
|---|---|
| Blank group G01 | Cell culture medium |
| Control group G02 | Cell culture medium + 0.5 mM $H_2O_2$ |
| Experimental group G30 | Cell culture medium + 0.5 mM $H_2O_2$ + 0.03125 mg/ml cashew testa extract obtained in example 1 |
| Experimental group G32 | Cell culture medium + 0.5 mM $H_2O_2$ + 0.0625 mg/ml cashew testa extract obtained in example 1 |

TABLE 3

| Group | Experimental culture medium |
|---|---|
| Blank group G01 | Cell culture medium |
| Control group G02 | Cell culture medium + 0.5 mM $H_2O_2$ |
| Experimental group G34 | Cell culture medium + 0.1 mM gallic acid obtained in example 2 + 0.5 mM $H_2O_2$ |
| Experimental group G36 | Cell culture medium + 0.1 mM gallocatechin obtained in example 2 + 0.5 mM $H_2O_2$ |
| Experimental group G38 | Cell culture medium + 0.1 mM epicatechin gallate obtained in example 2 + 0.5 mM $H_2O_2$ |
| Experimental group G40 | Cell culture medium + 0.1 mM epicatechin coumarin ester obtained in example 2 + 0.5 mM $H_2O_2$ |
| Experimental group G42 | Cell culture medium + 0.1 mM phloroglucinol obtained in example 2 + 0.5 mM $H_2O_2$ |
| Experimental group G44 | Cell culture medium + 0.1 mM protocatechuic acid obtained in example 2 + 0.5 mM $H_2O_2$ |
| Experimental group G46 | Cell culture medium + 0.1 mM naringenin 7-O-(6''-O-p-coumaryl)-β-D-glucoside obtained in example 2 + 0.5 mM $H_2O_2$ |

3. After treatment for 1 h, a DCFH-DA treatment reagent was added in each group so that the final concentration of each group was 5 μg/mL, and each group was treated at 37° C. for 15 min.

4. After treatment for 15 min, 100 mM of 5 μl/well $H_2O_2$ aqueous solution was added, and each group was treated at 34° C. for 0.5 h.

5. The treated experimental culture medium in each group was removed, and washed 2 times with 1× DPBS.

6. After washing, 500 μl of trypsin was added into each well for 5 min of photophobic reaction. After the reaction, the cell culture medium was added to terminate the reaction. After that, suspended cells and cell culture media in each well were collected into corresponding 1.5 ml micro-centrifuge tubes, and centrifuged for 5 min at 400×g to make cells in each centrifuge tube participated.

7. Supernatant in a centrifuge test tube for each group was removed, and the precipitate cells were washed with 1×DPBS once, and then centrifuged for 5 min at 400×g. The supernatant in a centrifuge test tube for each group was removed again, and 200 μl of 1× DPBS was added into the centrifuge test tube for each group to resuspend the cells so as to form a cell suspension.

8. The excitation light parameter of flow cytometry was set as 450-490 nm, the scattered light parameter of flow cytometry was set as 510-550, and then the fluorescence signal of DCFH-DA in each group was detected by flow cytometry. After entering the HFDPC cells, DCFH-DA was hydrated into DCFH (dichlorodihydrofluorescein) and then oxidized into DCF (dichlorofluorescein) capable of emitting green fluorescence by reactive oxygen species (ROS), the fluorescence intensity of the HFDPC cells treated by DCFH-DA can reflect the content of ROS in CCD-996SK cells, so as to obtain the proportion of highly expressed ROS cells in FDPC cells accounting for the number of original cells.

C. Test Results:

The relative ROS generation amounts of all groups are calculated according to the following formula: ROS relative generation amount (%)=(green fluorescence signal in each group/green fluorescence signal in blank group G01)×100%.

Since the experiment was repeated for three times, the measurement results of experiment that was repeated for three times were averaged as an average value, and then statistically significant differences between rest results of control group G02 and other groups were obtained by student's t-test statistical analysis. In the figures, "*" represents that compared with control group G02, p is less than 0.05, "" represents that compared with control group G02, p is less than 0.01, and "*" represents that compared with control group G02, p is less than 0.001.

Figure 9:
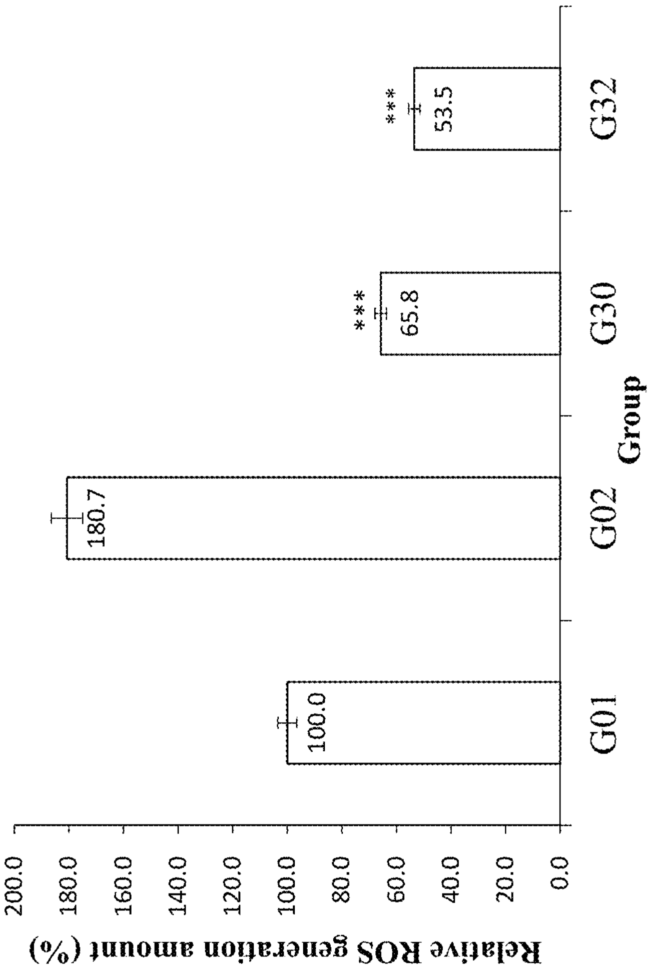
FIG. 9 is a bar chart showing a cell experiment result of relative reactive oxygen species (ROS) generation amounts of a cashew testa extract.

Refer to FIG. 9. The cells in blank group G01 were neither treated with the cashew testa extract, nor stimulated by adding $H_2O_2$. Thus, the test results in blank group G01 represent the expression of the cells under the condition of normal physiological metabolism. Therefore, under the condition that the relative ROS generation amount of blank group G01 was set as 100%, the relative ROS generation amount of control group G02 was 180.7%; the relative ROS generation amount of experimental group G30 was 65.8%, and the relative ROS generation amount of experimental group G32 was 53.5%. That is to say, relative to blank group G01, the cells in control group G02 were stimulated after addition of $H_2O_2$, and the relative ROS generation amount of control group G02 was increased by about 80.1%. Relative to control group G02, experimental group G30 was stimulated by adding $H_2O_2$ after addition of a low-concentration cashew testa extract, leading to significant reduction in relative ROS generation amount by about 63.5%. Relative to blank group G01, the relative ROS generation amount of experimental group was reduced by about 34.2% (ROS inhibition rate is as shown in Table 4 below). Relative to control group G02, experimental group G32 was stimulated by adding $H_2O_2$ after addition of a low-concentration cashew testa extract, leading to significant reduction in relative ROS generation amount by about 70.4%. Relative to blank group G01, the relative ROS generation amount of experimental group 1 was reduced by about 46.5% (ROS inhibition rate is as shown in Table 4 below).

TABLE 4

| Group | ROS inhibition rate relative to control group G02 | ROS inhibition rate relative to blank group G01 |
|---|---|---|
| Experimental group G30 | 63.5% | 34.2% |
| Experimental group G32 | 70.4% | 46.5% |

Figure 10:
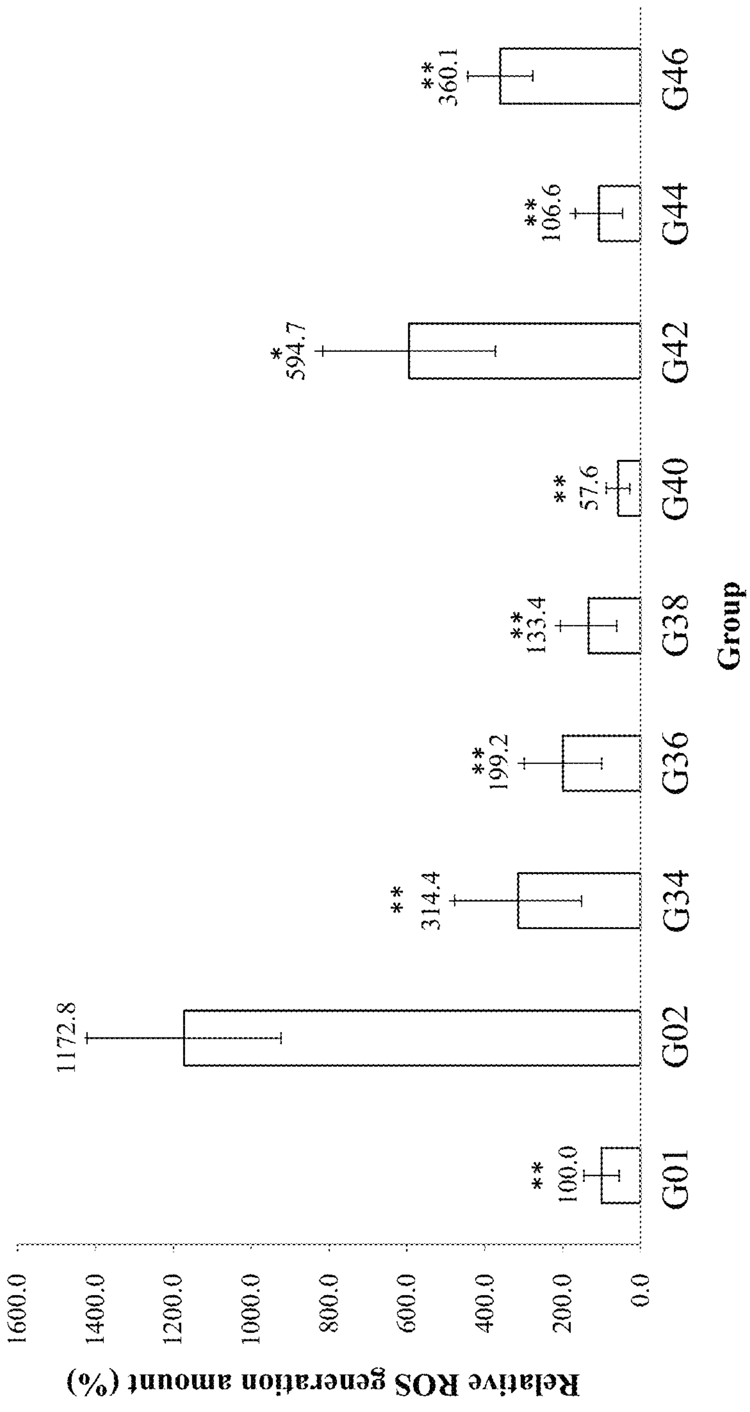
FIG. 10 is a bar chart showing a cell experiment result of relative ROS generation amounts of compounds of the cashew testa extract.

Refer to FIG. 10. The cells in blank group G01 were neither treated with the cashew testa extract, nor stimulated by adding $H_2O_2$, and therefore the test results in blank group G01 represent the expression of cells under the condition of normal physiological metabolism, and the relative ROS generation amount of each group is as shown in FIG. 10. Therefore, the ROS inhibition rate (%) of each group is calculated according to the following formula: (ROS generation amount of control group G02-ROS generation amount of blank group G01)−(ROS generation amount of experimental group-ROS generation amount of blank group G01)÷(ROS generation amount of control group G02-ROS generation of blank group G01. The ROS inhibition rate results of experimental group are as shown in Table 5 below.

TABLE 5

| Group | ROS inhibition rate relative to control group G02 |
|---|---|
| Experimental group G34 | 80.0% |
| Experimental group G36 | 90.8% |
| Experimental group G38 | 96.9% |
| Experimental group G40 | 100% |
| Experimental group G42 | 53.9% |
| Experimental group G44 | 99.4% |
| Experimental group G46 | 75.8% |

Accordingly, the cashew testa extract can significantly reduce the ROS generation amount of hair follicle cells caused by $H_2O_2$. $H_2O_2$ can induce aerobic metabolism of cells, so as to generate ROS. The ROS in cells can attack macromolecules such as proteins, nucleic acids and lipids, so as to cause cell damage. In other words, it is proven by the experiment that the cashew testa extract and its compounds are capable of promoting the antioxidant ability of hair follicle cells, and reducing hair follicle cell damage. The cashew testa extract has the effects of promoting the antioxidant activity and reducing cell damage.

Example 4: Test for Promoting Hair Follicle Cell Proliferation

A. Materials and Instruments:

1. Assay kit: cell proliferation assay kit (Click-iT™ Plus EdU Flow Cytometry Assay Kits-Alexa Fluor™ 488 picolyl azide, 50 tests), which is purchased from Invitrogen, with a product number C10632.

2. Flow cytometry (which is purchased from BD company with a product number BD Accuri).

B. Test Procedure:

1. HFDPC cells were inoculated into a 6-well culture medium at the density of $1\times10^5$ cells/well, and cultured under the conditions of 5% $CO_2$ and 37° C. until 80%-90% of cell fullness were achieved. Therefore, the HFDPC cells were divided into various groups, as shown in Table 6 and Table 7.

TABLE 6

| Group | Experimental culture medium |
|---|---|
| Blank group G01 | Cell culture medium |
| Positive control group G02 | Cell culture medium + 20% fetal bovine serum |
| Experimental group G30 | Cell culture medium + 20% fetal bovine serum + 0.125% cashew testa extract obtained in example 1 |
| Experimental group G32 | Cell culture medium + 20% fetal bovine serum + 0.25% cashew testa extract obtained in example 1 |

TABLE 7

| Group | Experimental culture medium |
|---|---|
| Blank group G01 | Cell culture medium |
| Positive control group G02 | Cell culture medium + 20% fetal bovine serum |
| Experimental group G34 | Cell culture medium + 0.1 mMgallic acid obtained in example 2 + 20% fetal bovine serum |
| Experimental group G36 | Cell culture medium + 0.1 mMgallocatechin obtained in example 2 + 20% fetal bovine serum |
| Experimental group G38 | Cell culture medium + 0.1 mM epicatechin gallate obtained in example 2 + 20% fetal bovine serum |
| Experimental group G40 | Cell culture medium + 0.1 mMe picatechin coumarin ester obtained in example 2 + 20% fetal bovine serum |
| Experimental group G42 | Cell culture medium + 0.1 mM phloroglucinol obtained in example 2 + 20% fetal bovine serum |

TABLE 7-continued

| Group | Experimental culture medium |
|---|---|
| Experimental group G44 | Cell culture medium + 0.1 mM protocatechuic acid obtained in example 2 + 20% fetal bovine serum |
| Experimental group G46 | Cell culture medium + 0.1 mM naringenin 7-O-(6"-O-p-coumaryl)-β-D-glucoside obtained in example 2 + 20% fetal bovine serum |

2. After culture for 24 h, the content of DNA in each group was measured by using cell proliferation assay kit. Therefore, cells in each group were treated according to test procedures provided by the cell proliferation assay kit, then the excitation light parameter of flow cytometer was set as 450-490 nm, and the scattered light parameter of flow cytometer was set as 510-550 nm, and then EdU (5-ethynyl-2'-deoxyuridine) fluorescent signal of each group was detected by flow cytometer.

C. Test Results:

The proliferation rate of hair follicle cells in each group was based on the content of DNA in each group. The relative hair follicle cell proliferation rates of all groups are calculated according to the following formula: relative hair follicle cell proliferation rate (%)=(fluorescent signal of each group/fluorescent signal of blank group G01)×100%.

The statistically significant difference between test results of blank group G01 and other groups was obtained by student's t-test statistical analysis. In the figures, "*" represents that compared with blank group G01, p is less than 0.05, "" represents that compared with blank group G01, p is less than 0.01, and "*" represents that compared with blank group G01, p is less than 0.001.

Figure 11:
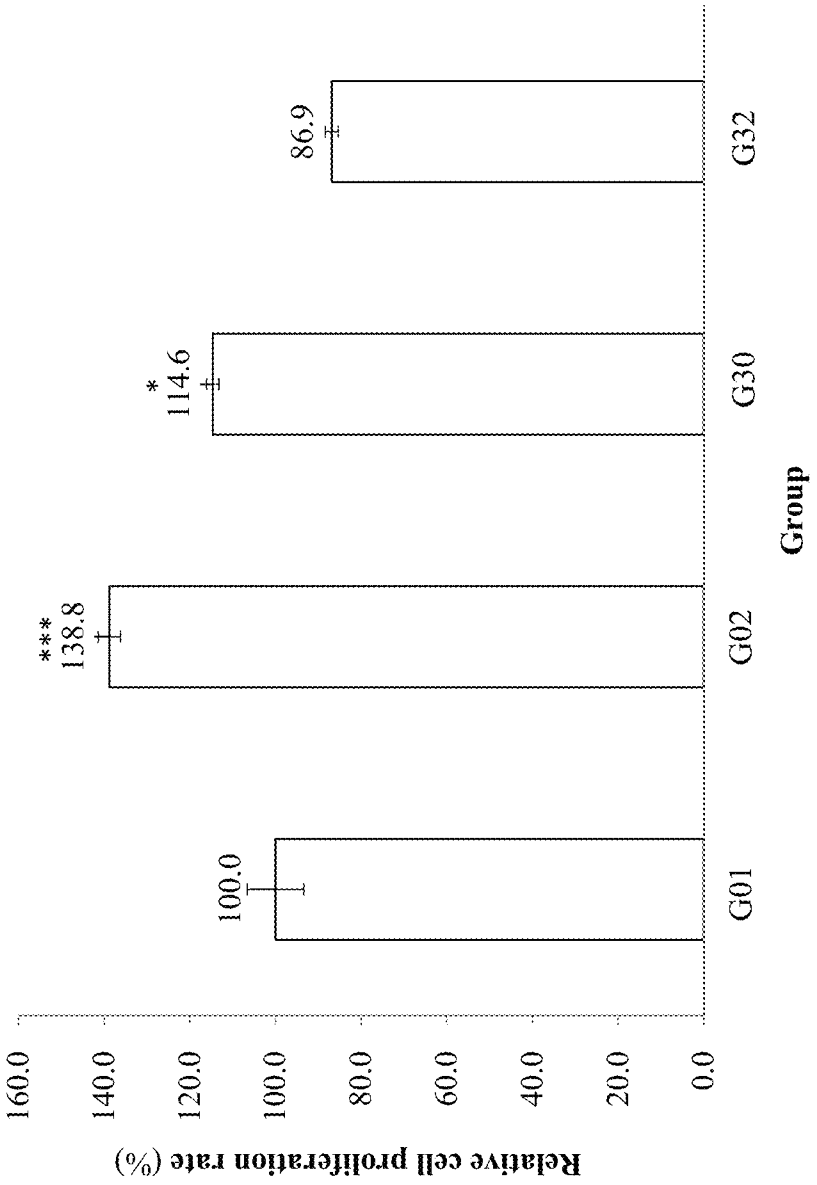
FIG. 11 is a bar chart showing a cell experiment result of relative cell proliferation rates of a cashew testa extract.

Refer to FIG. 11. Blank group G01 was not treated with the cashew testa extract, and therefore the test results of blank group G01 represent the expression of HFDPC cells under the condition of normal physiological metabolism. Therefore, under the condition that the relative hair follicle cell proliferation rate in blank group G01 was set as 100%, the relative hair follicle cell proliferation rate of control group G02 was 138.8%; the relative hair follicle cell proliferation rate of experimental group G30 was 114.6%; the relative hair follicle cell proliferation rate of experimental group G32 was 86.9%. That is to say, relative to blank group G01, the relative hair follicle cell proliferation rate of the HFDPC cells in control group G02 was significantly increased by about 38.8% after addition of 20% fetal bovine serum. Relative to blank group G01, the relative hair follicle cell proliferation rate of the HFDPC cells in experimental group G30 was significantly increased by about 14.6% after addition of 0.125% of cashew testa extract.

Figure 12:
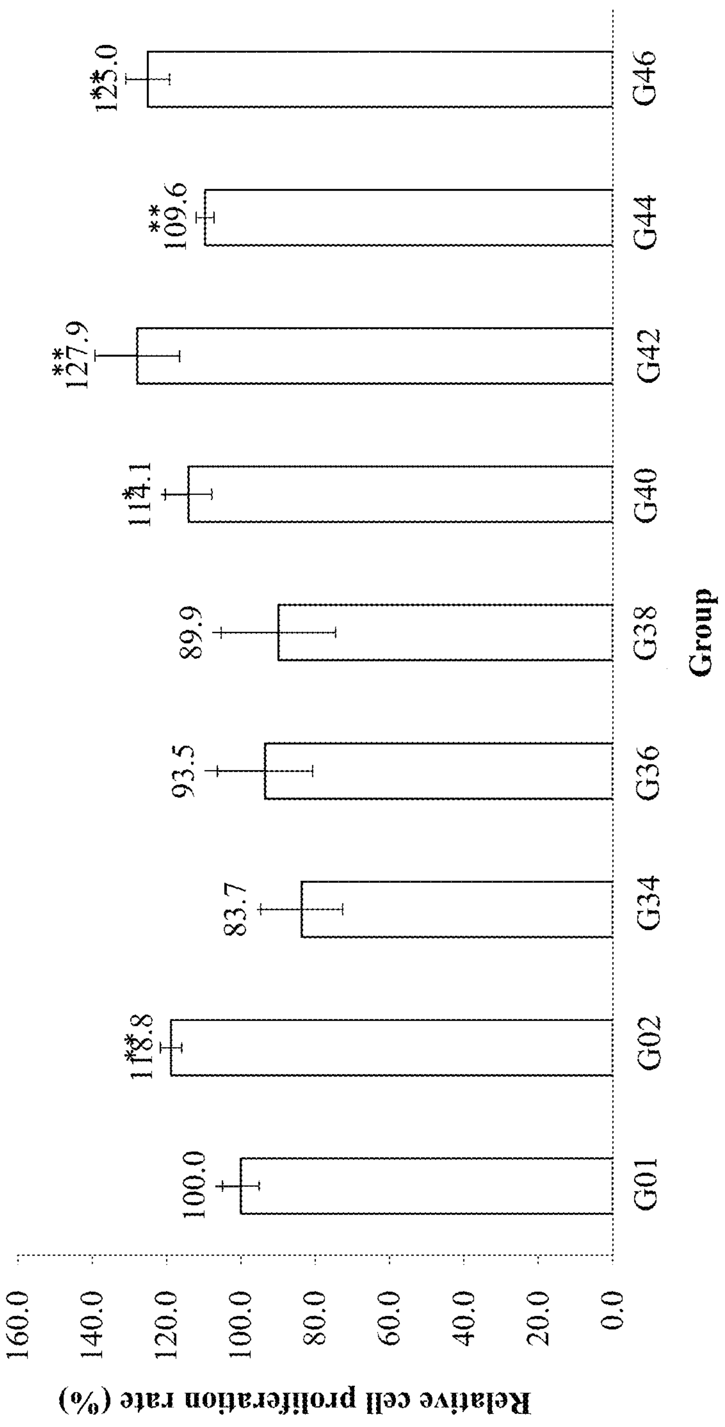
FIG. 12 is a bar chart showing a cell experiment result of relative cell proliferation rates of compounds of the cashew testa extract.

Refer to FIG. 12. Blank group G01 was not treated with the cashew testa extract, and therefore the test results of blank group G01 represent the expression of HFDPC cells under the condition of normal physiological metabolism. Therefore, under the condition that the relative hair follicle cell proliferation rate of blank group G01 was set as 100%, the relative hair follicle cell proliferation rate of control group G02 was 118.8%; the relative hair follicle cell proliferation rate of experimental group G34 was 83.7%; the relative hair follicle cell proliferation rate of experimental group G36 was 93.5%; the relative hair follicle cell proliferation rate of experimental group G38 was 89.9%; the relative hair follicle cell proliferation rate of experimental group G40 was 114.1%; the relative hair follicle cell proliferation rate of experimental group G42 was 127.9%; the relative hair follicle cell proliferation rate of experimental group G44 was 109.6%; the relative hair follicle cell proliferation rate of experimental group G46 was 125%. That is to say, relative to blank group G01, the relative hair follicle cell proliferation rate of the HFDPC cells in control group G02 was significantly increased by about 18.8% after addition of 20% fetal bovine serum. Relative to blank group G01, there was no significant difference between experimental groups G34-38; the relative hair follicle cell proliferation rates in experimental groups G40-46 were significantly increased by about 14.1%, 27.9%, 9.6% and 25%.

From experimental results, it can be seen that 0.125% cashew testa extract and experimental group G40-experimental group G46 can significantly promote the proliferation of hair follicle cells. Furthermore, the proliferation effects of experimental group G42 and experimental group G46 promoting the proliferation rate of hair follicle cells are superior to that of control group G02. In other words, it is proven by the experiment that the cashew testa extract and its compounds are capable of promoting the proliferation of hair follicle cells and promoting the growth of hairs, and then are used for hair care.

Example 5: Test on Cashew Testa Extract on Hair Care Related Gene Expression

A. Materials and Instruments:

1. RNA extraction kit, which is purchased from Genemark company.

2. SuperScript® III reverse transcriptase, which is purchased from Invitrogene company.

3. ABI StepOnePlus™ Real-Time PCR system, which is purchased from Thermo Fisher Scientific company.

4. KAPA SYBR FAST qPCR Master Mix (2×) Kit, which is purchased from KAPA Biosystems company, with a product number KK4600.

B. Test Procedure:

HFDPC cells were inoculated into a 6-well culture medium with 2 ml of cell culture medium in each well at the density of $1\times10^5$ cells, and cultured at 37° C. for 24 h.

After culture, the HFDPC cells were divided into several blank groups G01 and experimental groups, so as to respectively conduct comparison for different gene expressions. Where, the culture solution in blank group G01 contains no any extracts, the culture solutions in experimental groups G30 and G32 contain 0.125% and 0.25% of cashew testa extract prepared in example 1. Subsequently, each group was cultured for 6 h, 24 h and 48 h at 37° C.

The culture solutions in blank group G01 and experimental groups having different concentrations were removed, and washed with PBS.

After washing, the cell membranes of the HFDPC cells in each group were broken by using cell lysate of RNA extraction kit to form a cell solution.

RNA in the cell solution of each group was respectively extracted with the RNA extraction kit.

2000 ng of extracted RNA in each group was used as a template, and subjected to reverse transcription by SuperScript® III reverse transcriptase to form corresponding cDNA.

cDNA was respectively subjected to quantitative real-time reverse transcription polymerase chain reaction by using ABI StepOnePlus™ Real-Time PCR system, KAPA SYBR FASTqPCR Master Mix (2×) Kit and a combined primer in Table 8 to observe the expressions of target genes of HFDPC cells in blank group G01 and experimental groups and melting curves thereof. The setting conditions for an instrument for quantitative real-time reverse transcription polymerase chain reaction were as follows: react for 20 s at 95° C., react for 3 s at 95° C., react for 30 s at 60° C., and repeat 40 cycles.

The relative expression of the target gene was measured by using a $2^{-\Delta\Delta Ct}$ method. The relative expression is defined as multiple variation of RNA expression of a target gene of experimental group relative to RNA expression of the same gene of blank group G01. By the $2^{-\Delta\Delta Ct}$ method, the multiple variation is calculated according to the following formula based on a cycle threshold of a TBP gene as a cycle threshold (Ct) of a reference gene of internal control:

$$\Delta Ct = Ct_{target\ gene\ of\ experimental\ group/target\ gene\ of\ blank\ group\ G01} - Ct_{GAPDH}$$

$$\Delta\Delta Ct = \Delta Ct_{target\ gene\ of\ experimental\ group} - Ct_{target\ gene/blank\ group\ G01}$$

$$\text{Multiple variation} = 2^{-\Delta\Delta Ct\ average}$$

The standard deviation of relative expression is calculated by STDEV in Excel. The statistically significant difference between test results of blank group G01 and other groups is obtained by student's t-test statistical analysis. In the figures, "*" represents that compared with blank group G01, p is less than 0.05, "" represents that compared with blank group G01, p is less than 0.01, and "*" represents that compared with blank group G01, p is less than 0.001.

Experiment related sequences for related gene expression in Table 8 below.

TABLE 8

| Primer name | Sequence number | Sequence |
|---|---|---|
| SRD5α1-F | SEQ ID NO: 1 | TACGGGCATCGGTGCTTAAT |
| SRD5α1-R | SEQ ID NO: 2 | GCCATTGTACACGCCAACAG |
| SRD5α2-F | SEQ ID NO: 3 | TGCCTTCCTTCGCGGTG |
| SRD5α2-R | SEQ ID NO: 4 | CACAAATGTCCTGTGGAAGTAAT |
| AR-F | SEQ ID NO: 5 | GGTGAGCAGAGTGCCCTATC |
| AR-R | SEQ ID NO: 6 | GCAGTCTCCAAACGCATGTC |
| KROX20-F | SEQ ID NO: 7 | TTTGTGCACCAGCTGTCTGA |
| KROX20-R | SEQ ID NO: 8 | TTGATCATGCCATCTCCGGC |
| SCF-F | SEQ ID NO: 9 | CAGTAGCAGTAATAGGAAGGCCA |
| SCF-R | SEQ ID NO: 10 | AAGGCTCCAAAAGCAAAGCC |
| VEGF-F | SEQ ID NO: 11 | AGGGCAGAATCATCACGAAGT |
| VEGF-R | SEQ ID NO: 12 | AGGGTCTCGATTGGATGGCA |
| IGF1-F | SEQ ID NO: 13 | GCTCTTCAGTTCGTGTGTGGA |
| IGF1-R | SEQ ID NO: 14 | GCCTCCTTAGATCACAGCTCC |
| TGF-β-F | SEQ ID NO: 15 | CAATTCCTGGCGATACCTCAG |
| TGF-β-R | SEQ ID NO: 16 | GCACAACTCCGGTGACATCAA |

Therefore, the statistically significant difference between measurement results of blank group G01 and experimental groups is obtained by student's t-test statistical analysis. (In the figures, "*" represents that compared with control group G01, p is less than 0.05, "" represents that compared with control group G01, p is less than 0.01, and "" represents that compared with control group G01, p is less than 0.001. The more "*" represents the more significant statistical difference).

Figure 13:
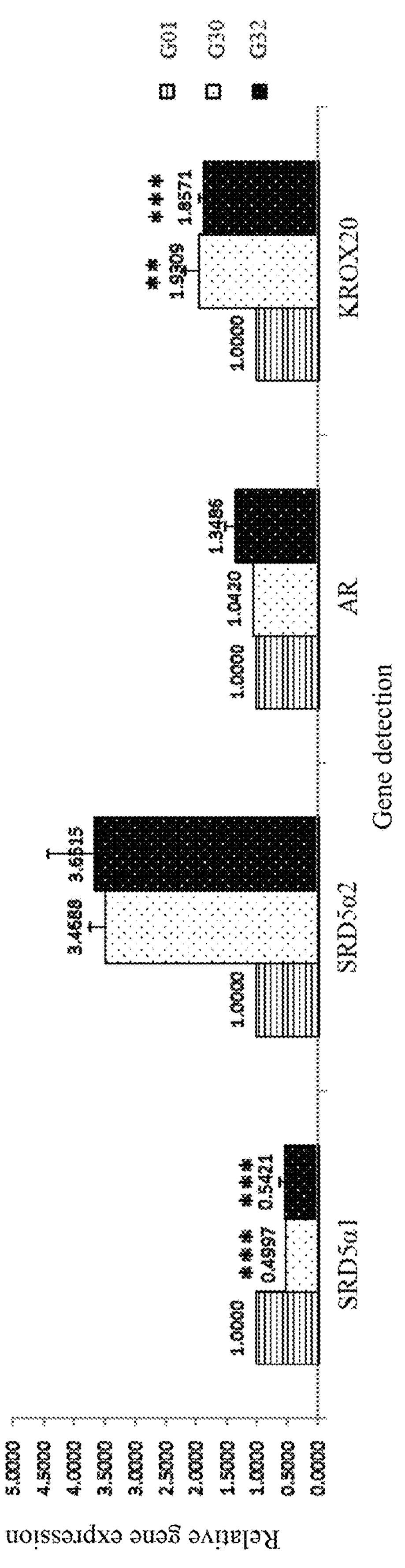
FIG. 13 is a bar chart showing a cell experiment result of relative gene expression levels (at 6 h) of a cashew testa extract.
Figure 14:
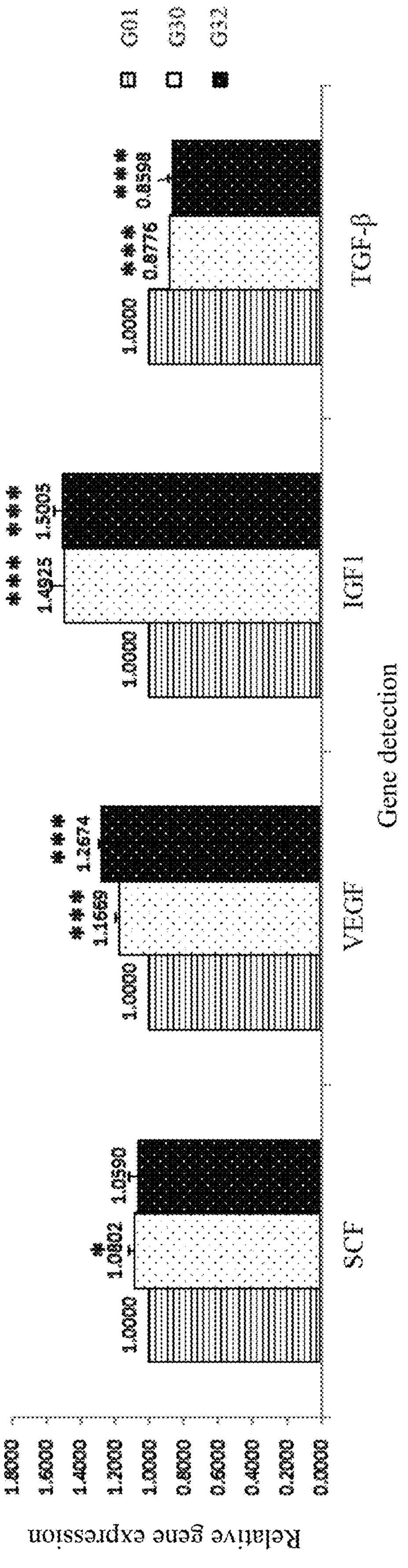
FIG. 14 is a bar chart showing a cell experiment result of relative gene expression levels (at 6 h) of a cashew testa extract.

After culture for 6 h, gene test results refer to FIG. 13 and FIG. 14. The HFDPC cells in blank group G01 were not subjected to any treatment, i.e., the expression of their genes was set as 1.0 under the condition of normal physiological metabolism. The expressions of SRD5α1 genes in SRD5α1 gene experimental group were as −0.49 times and −0.54 times as that of blank group G01. The expressions of SRD5α2 genes in SRD5α2 gene experimental group were as 3.4 times and 3.65 times as that of blank group G01. The expressions of AR genes in AR gene experimental group were as 1.04 times and 1.3 times as that of blank group G01, respectively. The expressions of KROX20 genes in KROX20 gene experimental group were as 1.93 times and 1.85 times as that of blank group G01, respectively. The expressions of SCF genes in SCF gene experimental group were as 1.08 times and 1.05 times as that of blank group G01, respectively. The expressions of VEGF genes in VEGF gene experimental group were as 1.16 times and 1.26 times as that of blank group G01, respectively. The expressions of IGF1 genes in VEGF gene experimental group were as 1.49 times and 1.5 times as that of blank group G01, respectively. The expressions of TGF-β genes in TGF-β gene experimental group were as −0.87 times and −0.85 times as that of blank group G01, respectively.

Figure 15:
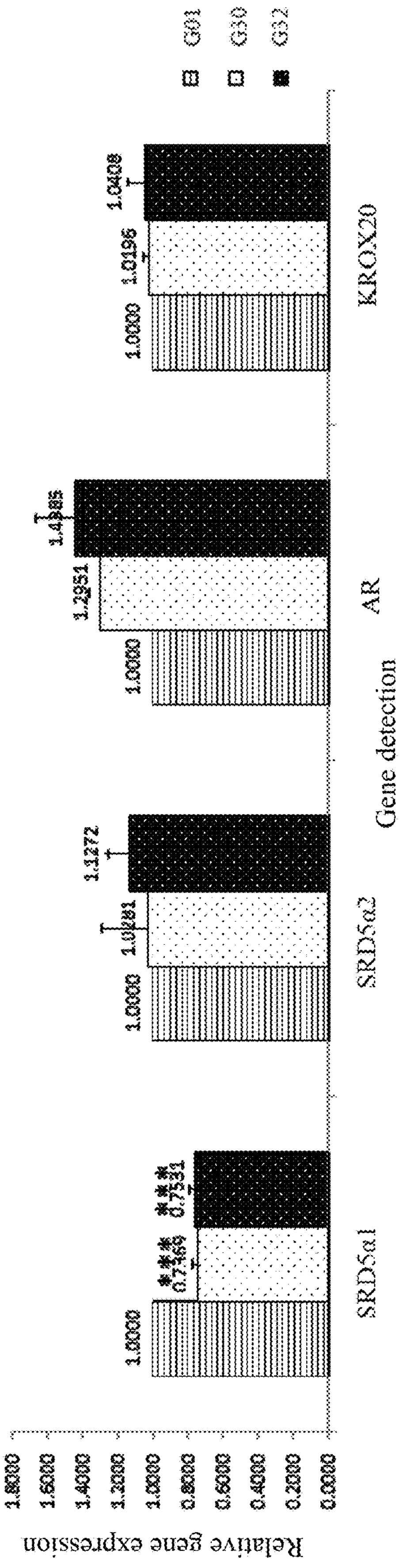
FIG. 15 is a bar chart showing a cell experiment result of relative gene expression levels (at 24 h) of a cashew testa extract.
Figure 16:
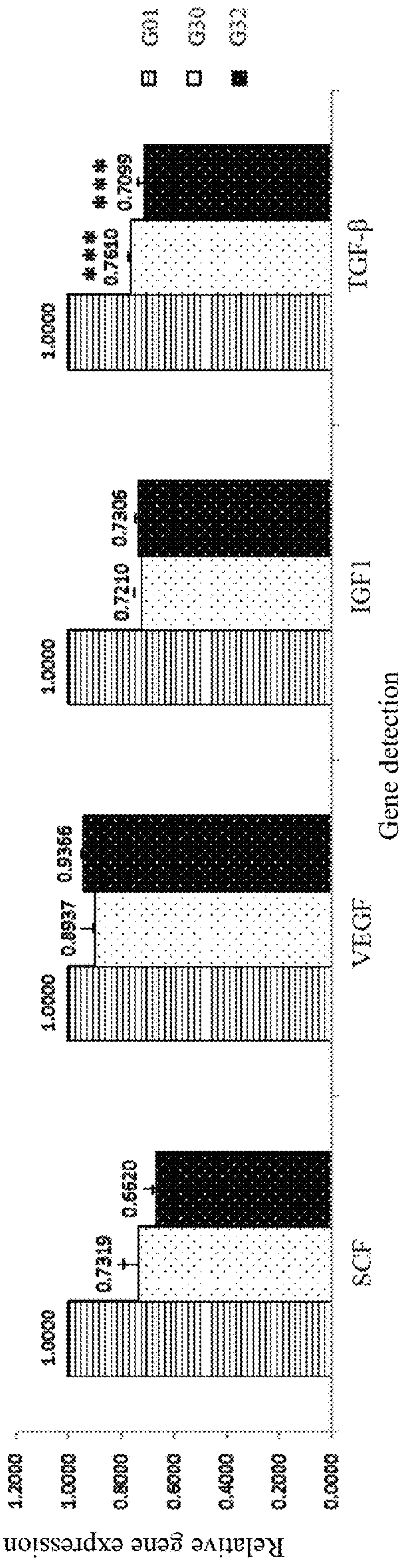
FIG. 16 is a bar chart showing a cell experiment result of relative gene expression levels (at 24 h) of a cashew testa extract.

After culture for 24 h, gene test results refer to FIG. 15 and FIG. 16. The HFDPC cells in blank group G01 were not subjected to any treatment, i.e., the expression of their genes was set as 1.0 under the condition of normal physiological metabolism. The expressions of SRD5α1 genes in SRD5α1 gene experimental group were as −0.73 times and −0.75 times as that of blank group G01, respectively. The expressions of SRD5α2 genes in SRD5α2 gene experimental group were as 1.02 times and 1.12 times as that of blank group G01, respectively. The expressions of AR genes in AR gene experimental group were as 1.29 times and 1.43 times as that of blank group G01, respectively. The expressions of KROX20 genes in KROX20 gene experimental group were as 1.01 times and 1.04 times as that of blank group G01, respectively. The expressions of SCF genes in SCF gene experimental group were as −0.73 times and −0.665 times as that of blank group G01, respectively. The expressions of VEGF genes in VEGF gene experimental group were as −0.89 times and −0.93 times as that of blank group G01, respectively. The expressions of IGF1 genes in IGF1 gene experimental group were as −0.76 times and −0.7 times as that of blank group G01, respectively. The expressions of TGF-β genes in TGF-β gene experimental group were as −0.76 times and −0.7 times as that of blank group G01, respectively.

Figure 17:
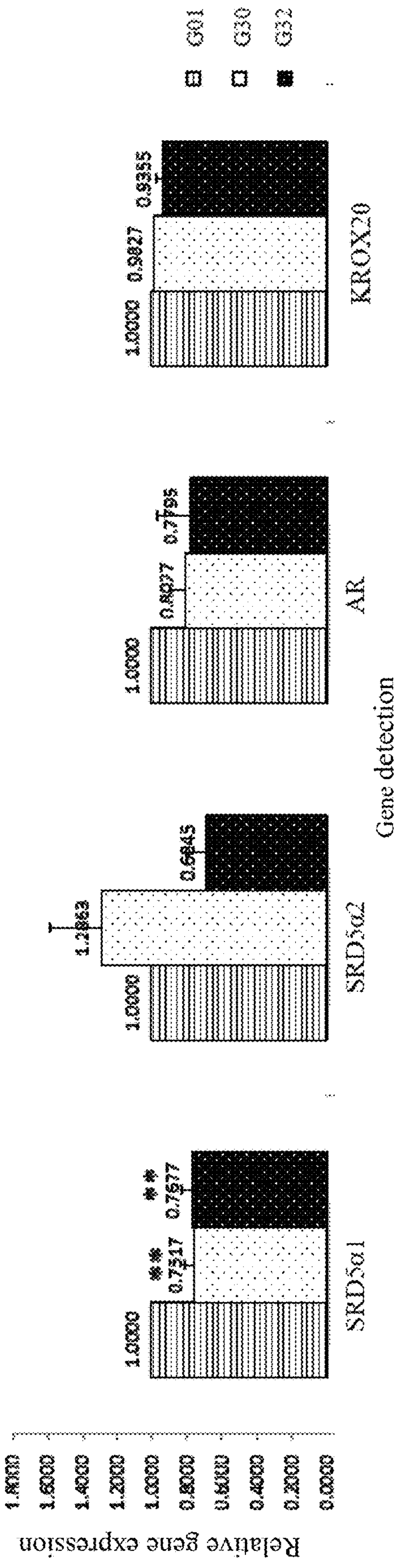
FIG. 17 is a bar chart showing a cell experiment result of relative gene expression levels (at 48 h) of a cashew testa extract.
Figure 18:
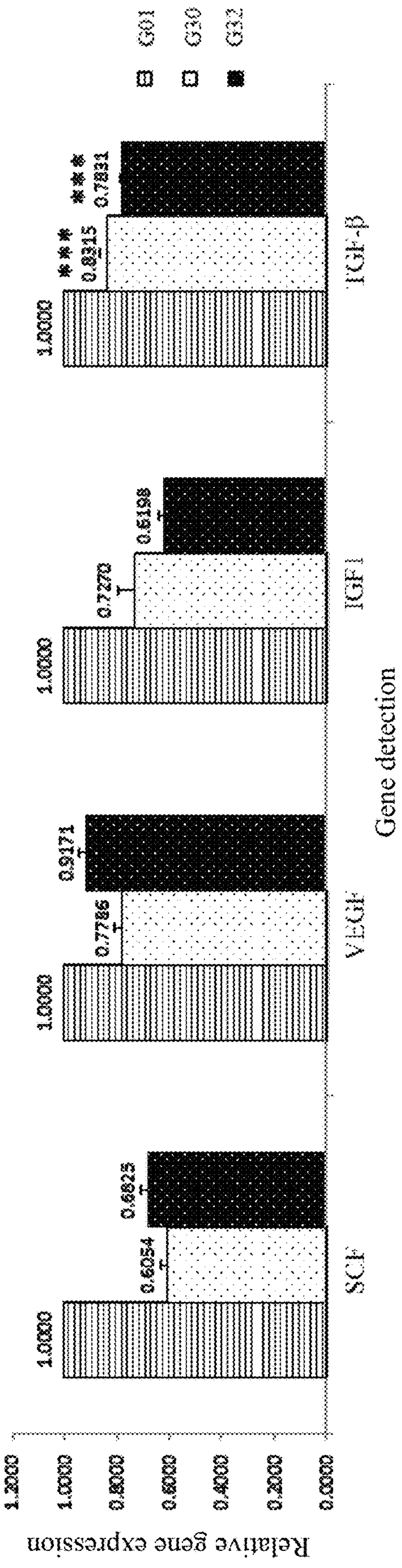
FIG. 18 is a bar chart showing a cell experiment result of relative gene expression levels (at 48 h) of a cashew testa extract.

After culture for 48 h, gene test results refer to FIG. 17 and FIG. 18. The HFDPC cells in blank group G01 were subjected to any treatment, i.e., the expression of their genes was set as 1.0 under the condition of normal physiological metabolism. The expressions of SRD5α1 genes in SRD5α1 gene experimental group were as −0.75 times and −0.76 times as that of blank group G01. The expression of SRD5α2 genes in SRD5α2 gene experimental group were as 1.2 times and −0.68 times as that of blank group G01, respectively. The expressions of AR genes in AR gene experimental group were as −0.8 times and −0.77 times as that of blank group G01, respectively. The expression of KROX20 genes in KROX20 gene experimental group were as −0.98 times and −0.93 times as that of blank group G01, respectively. The expressions of SCF genes in SCF gene experimental group were as −0.6 times and −0.68 times as that of blank group G01, respectively. The expressions of VEGF genes in VEGF gene experimental group were as −0.77 times and −0.91 times as that of blank group G01, respectively. The expressions of IGF1 genes in IGF1 gene experimental group were as −0.72 times and −0.61 times as that of blank group G01, respectively. The expressions of TGF-β genes in TGF-β gene experimental group were as −0.8 times and −0.78 times as that of blank group G01, respectively.

Statistical differences between hair care related genes and blank group G01 are as shown in Table 9 below.

TABLE 9

| Hair care related gene* | SRD5α1 | SRD5α2 | AR | KROX20 | SCF | VEGF | IGF1 | TGF-β |
|---|---|---|---|---|---|---|---|---|
| Blank group G01 6 hr | | | | | | | | |
| Experimental group G30 (0.125%) 6 hr | *** | | | ** | * | *** | *** | *** |
| Experimental group G32 (0.25%) 6 hr | *** | | | *** | | *** | *** | *** |
| Blank group G01 24 hr | | | | | | | | |
| Experimental group G30 (0.125%) 24 hr | *** | | | | | | | *** |
| Experimental group G32 (0.25%) 24 hr | *** | | | | | | | *** |
| Blank group G01 48 hr | | | | | | | | |
| Experimental group G30 (0.125%) 48 hr | ** | | * | | | | | *** |
| Experimental group G32 (0.25%) 48 hr | ** | ** | | | | | | *** |

Note:
SRD5α1, SRD5α2, AR and TGF-β are hair loss related genes; KROX20 and SCF are germinal related genes; VEGF and IGF1 are angiogenesis related genes.

Accordingly, the cashew testa extract can significantly inhibit the expressions of SRD5α1 genes, SRD5α2 genes, AR genes and TGF-β genes; significantly promote the expressions of KROX20 genes and SCF genes; and significantly promote the expressions of VEGF genes and IGF1 genes, indicating that the cashew testa extract can increase the hair follicle angiogenesis, promote the transportation of hair growth nutrients and promote the formation of hair follicles, thereby promoting the hair follicle health, reducing scalp oil production, reducing hair loss, reducing inflammation, and reducing hair loss caused by scalp inflammation, so as to improve hair follicle health.

Example 6: Human Body Test-Blood Detection

A. Test Procedure:

7 healthy adult subjects over 20 years old who have not taken or applied anti-hair loss related drugs or health products, and are aware of experiencing hair loss were administered with 1 bottle of 50 ml test beverage daily for 12 weeks in total (i.e., 84 days). The test beverage comprised 4 ml of cashew testa extract prepared in example 1, and the balance of water. Furthermore, the subjects were subjected to blood drawing at week 0, week 8 and week 12 to detect the variation of the concentrations of antioxidant index malondialdehyde in bloods before and after the cashew testa extract was taken.

This example was an outsourced testing for the concentration of antioxidant index malondialdehyde in the bloods of the subjects. The outsourced testing unit referred to the blood testing standards announced by the Ministry of Health and Welfare.

B. Test Results:

The statistically significant differences between test results at week 0, week 8 and week 12 were obtained by student's t-test statistical analysis. In the figures, "*" represents that compared with the week 0, p is less than 0.05, "" represents that compared with the week 0, p is less than 0.01, and "*" represents that compared with the week 0, p is less than 0.001.

Figure 19:
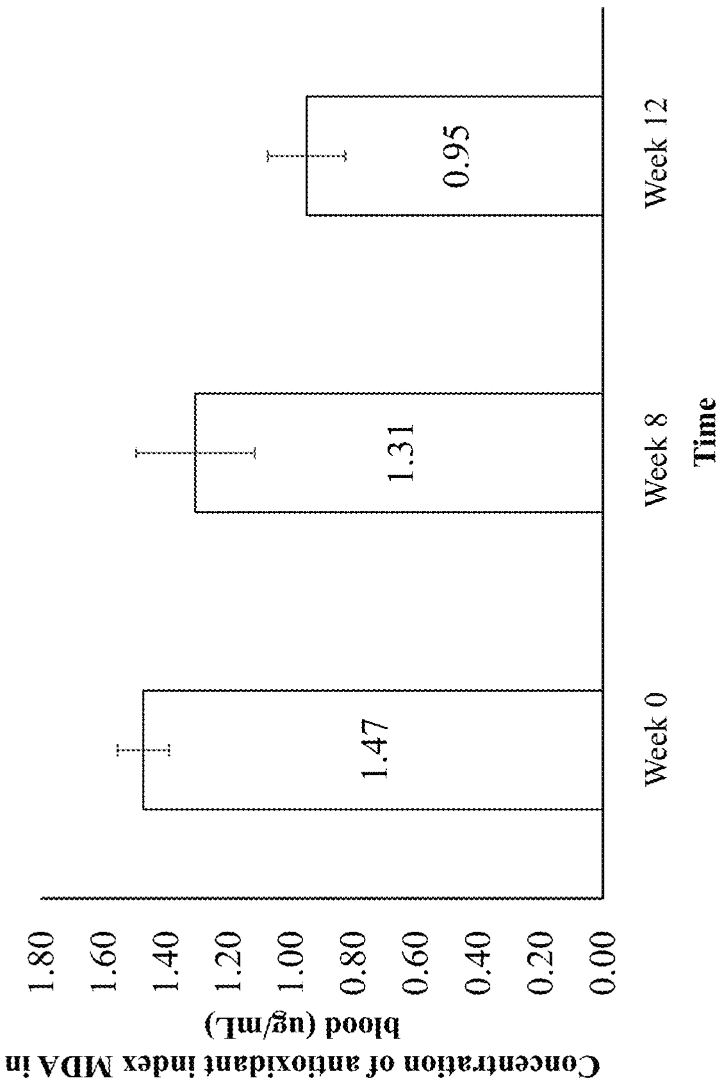
FIG. 19 is a bar chart showing a human body experiment result of concentrations of antioxidant index malondialdehyde (MDA) in blood at week 0, week 8 and week 12.

Refer to FIG. 19. The concentration of antioxidant index malondialdehyde in the blood of the subject at week 0 was about 1.47 μg/mL, the concentration of antioxidant index malondialdehyde in the blood of the subject at week 8 (i.e., after the cashew testa extract was continuously taken for 8 weeks) was significantly reduced by at least about 1.31 μg/mL, and the concentration of antioxidant index malondialdehyde in the blood of the subject at week 12 (i.e., after the cashew testa extract was continuously taken for 12 weeks) was significantly reduced by at least about 0.95 μg/mL. In other words, compared with a situation before taking, after continuously taking the cashew testa extract for 8 weeks can reduce the concentrations of malondialdehyde in bloods of these subjects were reduced by 11.4%; the continuous use of cashew testa extract for 12 weeks can reduce the blood malondialdehyde concentration of these subjects by 35.6%. Furthermore, the proportion of improved people was up to 100%. It indicates that the cashew testa extract can reduce the concentration of MDA in blood, promote the antioxidant ability of the body, so as to reduce hair follicle cell damage and promote hair follicle health.

Example 7: Human Body Test-Hair Diameter Detection

A. Test Procedure:

7 healthy adult subjects over 20 years old who have not taken or applied anti-hair loss related drugs or health products, and are aware of experiencing hair loss were administered with 1 bottle of 50 ml test beverage daily for 12 weeks in total (i.e., 84 days). The test beverage comprised 4 ml of cashew testa extract prepared in example 1, and the balance of water. Furthermore, the subjects were subjected to hair diameter detection at week 0, week 8 and week 12 to determine the variations of hair diameters before and after the cashew testa extract was taken.

In this example, detection was performed by using ASG-300/API-100 scalp detection instrument which was purchased from Huvis, Korea, with a unit being mm. The detection method is as follows: the diameters of the hairs at the same position of the top of the head that are distanced from the root of the hair by about 1 cm were calculated, and the average measurement value of the diameters of 3-5 hairs was adopted.

B. Test Results:

The statistically significant differences between test results at week 0, week 8 and week 12 were obtained by student's t-test statistical analysis. In the figures, "*" represents that compared with week 0, p is less than 0.05, "" represents that compared with week 0, p is less than 0.01, and "*" represents that compared with week 0, p is less than 0.001.

Figure 20:
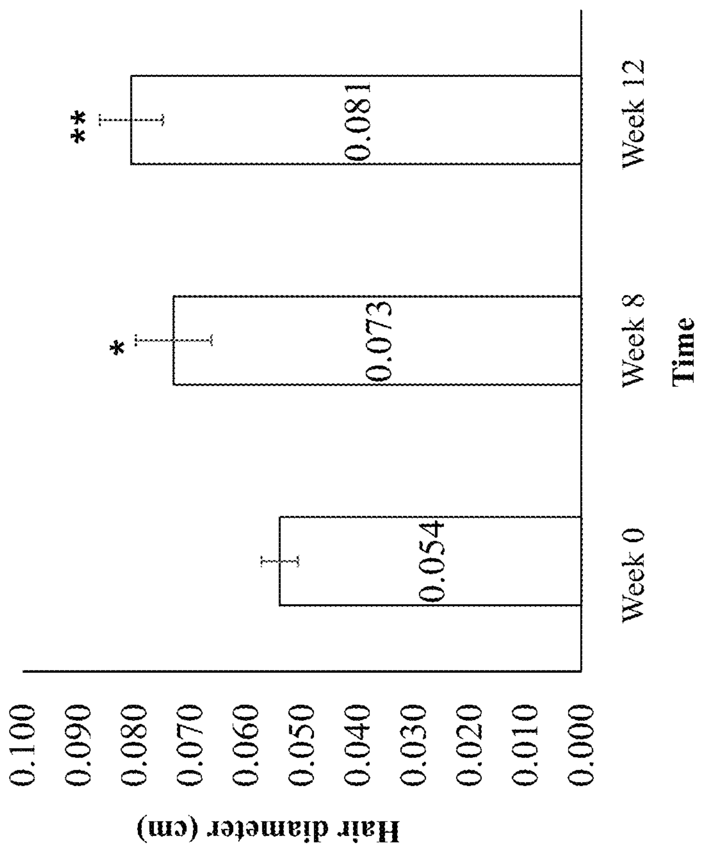
FIG. 20 is a bar chart showing a human body experiment result of hair diameter of subjects at week 0, week 8 and week 12.

Refer to FIG. 20. The diameter of the hair of the subject at week 0 was about 0.054 mm, the diameter of the hair of the subject at week 8 (i.e., the cashew testa extract was continuously taken for 8 weeks) was about 0.073 mm, the diameter of the hair of the subject at week 12 (i.e., the cashew testa extract was continuously taken for 12 weeks) was about 0.081 mm. In other words, compared with a situation before administration, the administration of the cashew testa extract for 8 weeks can make the diameters of hairs of these subjects significantly increased by 35.2%; the administration of the cashew testa extract for 12 weeks can make the diameters of hairs of these subjects significantly increased by 50%. Furthermore, the proportion of improved people was up to 100%. Accordingly, the cashew testa extract indeed can increase the diameter of the hair of the subject and enhance the stability of the hair, so as to promote hair follicle health.

In summary, the cashew testa extract in any example is obtained by extracting the cashew nut of *Anacardium occidentale* with a solvent, which can be used for preparing a hair care composition, so as to provide a composition capable of generating a hair care health effect on an individual when being administered to the individual. In some embodiments, provided is a method for hair care, comprising administering a subject in a need thereof a composition comprising a cashew testa extract. In some embodiments, in other words, the above composition has the function of hair care. In some embodiments, the composition prepared from the cashew testa extract also has one or more of the following functions: improving the antioxidant ability of hair follicle cells, promoting hair follicle angiogenesis, promoting the expression of hair growth genes, reducing the expression of hair loss genes, and increasing the diameter of the hair.

What is claimed is:

1. A method for hair care, comprising administering to a subject in need thereof a composition comprising an effective amount of a cashew testa extract, wherein the cashew testa extract is prepared by extracting a testa of cashew nut of *Anacardium occidentale*, and wherein the cashew testa extract improves hair follicle health.

2. The method according to claim 1, wherein in the extraction, a solid-to-liquid ratio of the cashew testa to a solvent is 5-20:1-5, an extraction temperature is 80° C. to 90° C., and an extraction time is 80 min to 120 min.

3. The method according to claim 1, wherein the cashew testa extract improves hair follicle health by improving an antioxidant ability of hair follicle cells.

4. The method according to claim 3, wherein the cashew testa extract comprises at least one compound selected from a group consisting of epicatechin coumaric acid ester, phloroglucinol, protocatechuic acid, and naringenin 7-O-(6"-O-p-coumaryl)-β-D-glucoside.

5. The method according to claim 1, wherein the cashew testa extract improves hair follicle health by promoting proliferation of hair follicle cells.

6. The method according to claim 5, wherein the cashew testa extract comprises at least one compound selected from a group consisting of epicatechin coumaric acid ester, phloroglucinol, protocatechuic acid, and naringenin 7-O-(6"-O-p-coumaryl)-β-D-glucoside.

7. The method according to claim 1, wherein the cashew testa extract improves hair follicle health by promoting hair follicle angiogenesis.

8. The method according to claim 1, wherein the cashew testa extract improves hair follicle health by promoting expression of germinal genes.

9. The method according to claim 1, wherein the cashew testa extract improves hair follicle health by reducing expression of hair loss genes.

10. The method according to claim 1, wherein the cashew testa extract improves hair follicle health by reducing a concentration of malondialdehyde (MDA) in blood.

11. The method according to claim 1, wherein the cashew testa extract has an ability of increasing a diameter of hair.

* * * * *